United States Patent
Okada et al.

(10) Patent No.: US 9,510,966 B2
(45) Date of Patent: Dec. 6, 2016

(54) KNEE BRACE, AND SET OF OUTER LEG JOINT AND INNER LEG JOINT

(75) Inventors: Takeshi Okada, Matsuyama (JP); Seiji Inoue, Matsuyama (JP)

(73) Assignee: AITORINO CO., LTD., Ehime (JP)

(*) Notice: Subject to any disclaimer, the term of this patent is extended or adjusted under 35 U.S.C. 154(b) by 270 days.

(21) Appl. No.: 13/978,937

(22) PCT Filed: Sep. 14, 2011

(86) PCT No.: PCT/JP2011/071047
§ 371 (c)(1),
(2), (4) Date: Jul. 10, 2013

(87) PCT Pub. No.: WO2012/098733
PCT Pub. Date: Jul. 26, 2012

(65) Prior Publication Data
US 2013/0289458 A1    Oct. 31, 2013

(30) Foreign Application Priority Data

Jan. 19, 2011    (JP) .................................. 2011-023307

(51) Int. Cl.
*A61F 5/01*    (2006.01)

(52) U.S. Cl.
CPC ........... *A61F 5/0123* (2013.01); *A61F 5/0102* (2013.01); *A61F 2005/0146* (2013.01); *A61F 2005/0148* (2013.01)

(58) Field of Classification Search
CPC ............ A61F 5/0123; A61F 2005/0148; A61F 5/0111; A61F 5/0585; A61F 5/00; A61F 5/01; A61F 5/0102; A61F 5/0106; A61F 2005/0146

(Continued)

(56) References Cited

U.S. PATENT DOCUMENTS 3,965,671 A * 6/1976 Kodera ............................. 59/80
4,320,747 A * 3/1982 Daniell, Jr. ..................... 602/16

(Continued)

FOREIGN PATENT DOCUMENTS

| JP | 3740638 B2 | 2/2006 |
| JP | 2006175143 A | 7/2006 |
| JP | 2010069059 A | 4/2010 |

OTHER PUBLICATIONS

Requisition by the Examiner dated Jul. 14, 2014, for Canadian patent application 2825290.

(Continued)

*Primary Examiner* — Alireza Nia
*Assistant Examiner* — Keri J Nelson
(74) *Attorney, Agent, or Firm* — Typha IP LLC

(57) ABSTRACT

A knee brace capable of correction only in a required angle range and of reproducing a normal screw-home movement in a knee joint of a knee osteoarthritis patient having outer and inner leg joints including first and second couplings coupled at coupling portions. The coupling portion includes a cam groove, a long groove, a rotation fulcrum shaft, and a cam shaft. When flexing the knee, the rotation fulcrum shaft and the cam shaft slide in the long groove and the cam groove and the second coupling rotates around the coupling portion with respect to the first coupling to flex the leg joints, and when extending the leg joints, the rotation fulcrum shaft and the cam shaft slide in the long groove and the cam groove to move the second coupling on the outer leg side upward and rearward and the second coupling on the inner leg side downward and forward.

9 Claims, 20 Drawing Sheets

(58) Field of Classification Search
USPC ............................................. 602/16, 23, 26
See application file for complete search history.

(56) References Cited

U.S. PATENT DOCUMENTS

| | | | |
|---|---|---|---|
| 4,556,053 A * | 12/1985 | Irons ..................... | A61F 5/0123 |
| | | | 602/16 |
| 4,723,539 A | 2/1988 | Townsend | |
| 5,009,223 A * | 4/1991 | DeFonce ......................... | 602/16 |
| 5,107,824 A * | 4/1992 | Rogers .................. | A61F 5/0123 |
| | | | 602/16 |
| 5,330,418 A | 7/1994 | Townsend et al. | |
| 5,611,774 A | 3/1997 | Postelmans | |

OTHER PUBLICATIONS

International Search Report in the corresponding International Patent Application No. PCT/JP2011/071047 issued Oct. 11, 2011.

\* cited by examiner

FIG. 19
(A)
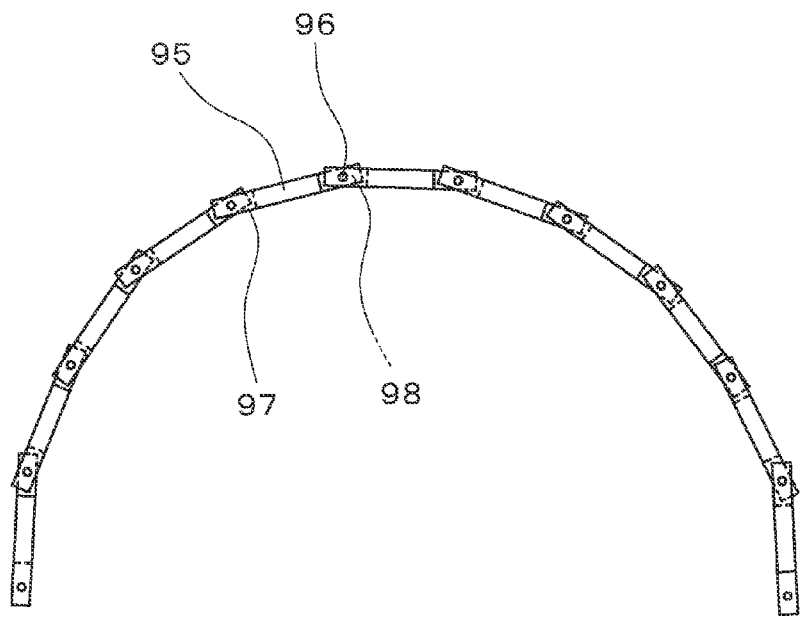
(B)
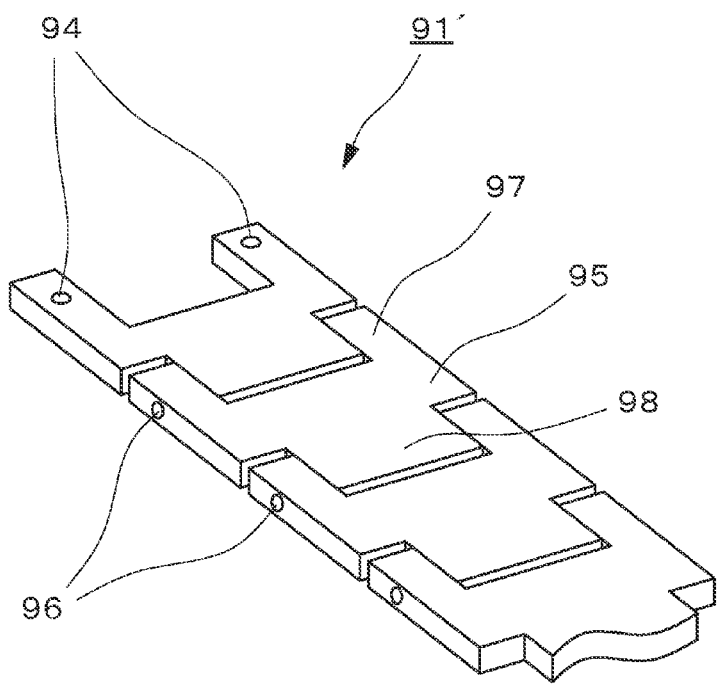

KNEE BRACE, AND SET OF OUTER LEG JOINT AND INNER LEG JOINT

TECHNICAL FIELD

The present invention relates to a knee brace and a set of an outer leg joint and an inner leg joint, and specifically to a knee brace and a set of the outer leg joint and the inner leg joint that corrects a movement of flexing a knee joint of a knee osteoarthritis patient accompanied by a bowleg or knock-knee.

BACKGROUND ART

As a typical example of a symptom accompanied by a pain in a knee joint, knee osteoarthritis is known. Knee osteoarthritis is a case in which a function of a knee joint is impaired by muscle weakness, aging, obesity, and the like, causing wear of knee cartilage, loose engagement of meniscus, deformity, rupture, excessive congestion of synovial fluid due to inflammation, and causes a pain when walking.

An advancement of the knee osteoarthritis may cause a varus deformity due to joint destruction, resulting in bowleg which is commonly called O-leg.

Bowleg is believed to be a cause of the knee osteoarthritis along with knock-knee, which is commonly called X-leg, intimately related to the knee osteoarthritis.

In the case of bowleg, a cartilage inside the knee joint tends to be damaged, and in the case of knock-knee, an outer cartilage tends to be damaged. As the state of the knee osteoarthritis advances accompanied by bowleg or knock-knee, leg curvature becomes severer to make an inclination of the crus still steeper, further wearing the joint cartilage. When bones rub each other directly due to the wear of the cartilage, a strong pain is felt disabling a walk.

To treat the knee osteoarthritis, an operative treatment of sectioning a knee joint and implanting a metallic artificial joint, and a conservative treatment of continuing a rehabilitation using a gait training equipment to recall a memory of correct walking behavior, are known.

With the operative treatment, though the pain of walking is eliminated, there is a drawback that the patient can sit only on a chair due to a narrow rotation angle of the artificial joint and that the patient cannot stand up if both legs have the artificial joint. Another drawback is that the useful life is approximately 10 years because aging may weaken the bone and lose strength balance with metal and therefore a further surgery will be required after the useful life. Furthermore, the operative treatment is expensive.

On the other hand, the conservative treatment is a long-term treatment of relieving the pain while walking using a knee brace and enhancing muscles by regularly walking every day, which requires physical strength and patience of the patient, but does not present the drawbacks unique to the operative treatment.

Accordingly, various knee braces for the conservative treatment have been conceived (see, for example, Patent Document 1).

However, because the knee brace according to Patent Document 1 uses a rack and a gear in joint members on the outer leg side and the inner leg side, the total weight of the knee brace is heavy. Furthermore, a gear sound occurs when walking with the knee brace mounted, imparting discomfort to the patient wearing it.

Moreover, because the joint members on the outer leg side and the inner leg side both use the rack and the gear, not only the correction effect is exerted over an angle range that does not need to be corrected but also the correction is made in an opposite direction within 90-degree flexion, which prevents a smooth movement of the knee.

Now, a relation between the movement of the knee joint in a knee osteoarthritis patient with bowleg or knock-knee and the angle range that needs to be corrected is shown in FIG. 20.

FIG. 20(C) depicts a 90-degree flexed state when sitting on a chair, and FIG. 20(D) depicts a fully flexed state when sitting on heels. Generally the angle between the femur and the crus is about 18 degrees when sitting on heels as depicted in FIG. 20(D), where the knees flex 162 degrees assuming 0 degree in an extended state. In a state of flexing more than 90 degrees, no force is applied to the knee joint and therefore no correction is required.

In the fully extended state when standing as depicted in FIG. 20(B), the angle of the knee is substantially 0 degree, where a force is applied to the knee joint and a correction is required.

In a walking state of a healthy person as depicted in FIG. 20(A), there is a repetition of about 6-degree flexed state of the front stepping foot and up to about 45-degree flexed state of the rear kicking foot, where the highest force is applied to the knee joint in the knee angle range of 0-45 degrees and a correction is required in this range.

As shown in FIG. 20, assuming the fully extended state of the knee as substantially 0 degree in the angle range of the knee osteoarthritis patient with bowleg or knock-knee, the flexing angle of the knee is between 0 and 45 degrees.

The knee brace according to Patent Document 1 uses the rack and the gear in the joint members on the outer leg side and the inner leg side, and therefore the correction effect on the knee joint is constant and linear. The correction effect is exerted over the entire angular range that can be achieved by the knee joint flexing, which in turn prevents a smooth movement of the knee at the flexing angle over 90 degrees causing such troubles as difficulty of sitting on a chair and disability of sitting on heels.

Patent Document 1: JP 2010-69059 A (claims 2, 3; paragraphs 0023-0026, 0034-0037; FIGS. 1, 10)

DISCLOSURE OF THE INVENTION

Problem to be Solved by the Invention

The present invention was made in the light of the above, an object of which is to provide a highly operable knee brace capable of correcting a knee joint of a knee osteoarthritis patient only in an angle range that requires correction.

Another object of the present invention is to provide a knee brace with a three-dimensional motion capable of reproducing not only a two-dimensional movement in a direction of raising a folded leg but also a screw-home movement of a healthy knee joint in the knee joint of the knee osteoarthritis patient by generating an outward twist when fully extending out the knee joint, using a simple structure.

Means for Solving Problem

According to the invention as in claim 1, the above problem is solved by a knee brace for a knee osteoarthritis patient including: a femur fixing means to be mounted on a femur of the patient; a crus fixing means to be mounted on a crus of the patient; and an outer leg joint and an inner leg joint respectively fixed to the crus fixing means and the femur fixing means at both ends and arranged on an outer leg side and an inner leg side of a knee joint of the patient for flexing; in which each of the outer leg joint and the inner leg joint includes a first coupling means to be arranged along a side of the femur and a second coupling means to be arranged along a side of the crus, the first coupling means and the second coupling means being coupled together by a coupling portion to be arranged at a side of the knee joint, the coupling portion includes a cam groove provided in the first coupling means or the second coupling means, a long groove provided in the second coupling means or the first coupling means, a rotation fulcrum shaft sliding in the long groove and provided in each of the first coupling means or each of the second coupling means, and a cam shaft sliding in the cam groove and provided to the second coupling means or the first coupling means, in which the rotation fulcrum shafts and the cam shafts slide in the long grooves and the cam grooves, respectively, when the patient flexes a knee, and thereby the second coupling means rotate around the coupling portions with respect to the first coupling means to flex the outer leg joint and the inner leg joint, and in which the rotation fulcrum shafts and the cam shafts slide in the long grooves and the cam grooves, respectively, when the outer leg joint and the inner leg joint extend, thereby the second coupling means on the outer leg side moves upward and rearward and the second coupling means on the inner leg side moves downward and forward.

According to the knee brace of the present invention configured as above, when the outer leg joint and the inner leg joint extend, by the rotation fulcrum shaft and the cam shaft sliding in the long groove and the cam groove, the second coupling means on the outer leg side moves upward and the second coupling means on the inner leg side moves downward allowing a small space in a site where a knee joint bone should contact to instantly relieve the knee pain when walking, which facilitates the gait training and allows for gradually enhancing the muscles through daily walking. Furthermore, because the knee brace leads to a correct walking trajectory, the gait training can be performed alone without being accompanied by a physical therapist.

Because the body remembers the correct walking trajectory and the muscles are enhanced by continuing the training, the patient can eventually return to the life without pain even if the knee brace is removed.

Because the coupling portion includes the cam groove provided in each of the first coupling means or each of the second coupling means, the long groove provided in each of the second coupling means or each of the first coupling means, the rotation fulcrum shaft sliding in the long groove and provided to each of the first coupling means or each of the second coupling means, and a cam shaft respectively sliding in the cam groove and provided to each of the second coupling means or each of the first coupling means, and is configured so that, when the patient flexes the knee, the rotation fulcrum shaft and the cam shaft slide in the long groove and the cam groove, respectively, thereby the second coupling means rotates around the coupling portion with respect to the first coupling means to flex the outer leg joint and the inner leg joint, it is not so heavy as the knee brace using the rack and the gear with reduced total weight and enables a smooth and quiet flexion of the leg, which can be worn on the leg without any uncomfortable feeling. Furthermore, by making the cam groove longer, the patient can even sit on heels with the knees flexed further than the right angle while wearing the knee brace according to the present invention.

Moreover, because it is configured so that the second coupling means on the outer leg side moves upward and rearward and the second coupling means on the inner leg side moves downward and forward by the rotation fulcrum shaft and the cam shaft sliding in the long groove and the cam groove, respectively, when the outer leg joint and the inner leg joint extend, the outer leg side of the patient's leg can be pulled upward and the inner leg side can be pulled downward, whereby the knee of the knee osteoarthritis patient with bowleg can be corrected in the direction of raising the flexed leg. Furthermore, because the outer leg side is pulled rearward and the inner leg side is pulled forward when the patient extends the leg, the correction can be performed so as to reproduce the correct screw-home movement.

Moreover, because the knee brace includes the femur fixing means, the crus fixing means, and the outer leg joint and the inner leg joint respectively fixed to the crus fixing means and the crus fixing means at both ends and arranged on the outer leg side and the inner leg side of the knee joint of the patient for flexing, the knee brace is configured to surround the knee from four directions and the periphery of the knee itself is open without any covering, whereby a tension state with a force applied and a relief state without the force applied occur to the knee joint alternately when the patient walks, enabling an enhancement of the muscles around the knee of the patient.

Furthermore, it is preferable that the cam groove is provided in the first coupling means, the long groove is provided in the second coupling means, the rotation fulcrum shaft is provided to the first coupling means, the shaft is provided to the second coupling means, the long groove on the outer leg side inclines with respect to the lengthwise direction of the second coupling means so that an end portion of the long groove at which the rotation fulcrum shaft is located when the outer leg joint extends is located on a front side of the patient, and the long groove on the inner leg side inclines with respect to the lengthwise direction of the second coupling means so that an end portion of the long groove at which the rotation fulcrum shaft is located when the inner leg joint extends is located on a rear side of the patient.

Due to this configuration, the second coupling means on the outer leg side can move rearward and the second coupling means on the inner leg side can move forward by the rotation fulcrum shaft and the cam shaft sliding in the long groove and the cam groove when the outer leg joint and the inner leg joint extend, consequently enabling reproduction of the correct screw-home movement when the patient extends the leg. While a healthy person causes a natural screw-home movement by the structure of the knee joint and the tension of the Achilles' tendon, the knee osteoarthritis patient lacks this movement. Therefore, by reproducing the screw-home movement in the knee of the knee osteoarthritis patient, the knee brace can lead to the correct walking trajectory that does not extend the skeleton too much.

Furthermore, while the knee brace using the rack and the gear needs to employ different gear ratios between right and left to reproduce the screw-home movement, resulting in a complex design of the rack and the gear, the present invention employs the configuration provided with the cam groove and the cam shaft that allow for reproduction of the screw-home movement only by adjusting the angle of inclination and length of the long groove, enabling the correction of the screw-home movement to be achieved by a simple configuration.

Moreover, it is preferable that the long groove inclines with respect to the lengthwise direction of the second coupling means so that a lower end is located anterior to an upper end, the rotation fulcrum shaft on the outer leg side is located at the upper end of the long groove when the outer leg joint flexes substantially at a right angle and located at the lower end of the long groove when the outer leg joint extends, and the rotation fulcrum shaft is located on the inner leg side at the lower end of the long groove when the inner leg joint flexes substantially at the right angle and located at the upper end of the long groove when the inner leg joint extends.

Due to this configuration, the second coupling means on the outer leg side can move rearward and the second coupling means on the inner leg side can move forward by the rotation fulcrum shaft and the cam shaft sliding in the long groove and the cam groove when the outer leg joint and the inner leg joint extend, consequently enabling reproduction of the correct screw-home movement when the patient extends the leg.

It is preferable that, when the outer leg joint flexes to the right angle, a distance r2 from a point in the cam groove on the outer leg side where the cam shaft on the outer leg side is located to the rotation fulcrum shaft on the outer leg side and a distance r1 from a lower end of the cam groove on the outer leg side to the rotation fulcrum shaft on the outer leg side are substantially the same as each other, and a distance r3 from an upper end of the cam groove on the outer leg side to the rotation fulcrum shaft on the outer leg side is longer than the distance r1 and the distance r2, and that, when the inner leg joint flexes at the right angle, a distance r5 from a point in the cam groove on the inner leg side where the cam shaft on the inner leg side is located to the rotation fulcrum shaft on the inner leg side and a distance r4 from the upper end of the cam groove on the inner leg side to the rotation fulcrum shaft on the inner leg side are substantially same as each other and a distance r6 from the lower end of the cam groove on the inner leg side to the rotation fulcrum shaft on the inner leg side is longer than the distance r4 and the distance r5.

Due to this configuration, because the rotation fulcrum shaft does not move while the cam shaft moves from the points of the distances r1 and r4 to the points of distances r2 and r5 when extending the flexed outer leg joint and the inner leg joint, and the rotation fulcrum shaft starts to move only when the cam shaft moves past the points of the distances r2 and r5, the correction effect by the knee brace does not work when the knee is greatly flexing like sitting on heels and the correction effect can start to work only when the knee extends more than a predetermined angle. As a result, a practical correction can be performed on the knee osteoarthritis with bowleg or knock-knee along with the actual condition that the correction is not required when deeply flexing but required only at flexion angles less than about 45 degrees that is closer to an extended state.

It is preferable that the cam groove on the outer leg side takes a curved shape convex forward and the cam groove on the inner leg side takes a curved shape convex rearward.

Due to this configuration, when the outer leg joint and the inner leg joint extend, by the rotation fulcrum shaft and the cam shaft sliding in the long groove and the cam groove, the second coupling means on the outer leg side can move upward and rearward, and the second coupling means on the inner leg side can move downward and forward.

It is preferable that the femur fixing means and the Crus fixing means include a rigid support portion supporting a part of each circumference of the femur and the crus and a soft coupling portion extending between both circumferential ends portions of the support portion, and that the support portion includes a folding portion extending in a lengthwise direction of the femur and the crus so that the support portion is foldable along the folding portion.

Due to this configuration, the patient can carry the knee brace in a bag and put it on as soon as the knee starts to ache. A novel rigid and compact knee brace different from the conventionally known soft supporter can be provided. Because the knee brace can be double folded at the center to be put in the bag with only one folding portion, the knee osteoarthritis patient can enjoy a travel or an excursion. Because the patient is not always wearing the knee brace on the knee, the knee brace can be folded and packed up when it is not used, thus providing a convenient knee brace.

Although a relatively mild-case patient tends to avoid a hard knee brace that may give a pathological impression, the present invention can provide a foldable knee brace which can achieve a hard knee brace with an impression similar to a soft supporter. Because a fancy hard knee brace with a sporty atmosphere can be provided, a new market can be expected targeting relatively mild-case patients and patients-to-be.

Furthermore, because the relatively mild-case patients and patients-to-be can be prevented from avoiding use of a hard knee brace, it is possible to prevent the symptom from advancing by starting the correction while the case is still mild.

Moreover, because the folding portion extends in the lengthwise direction of the femur and the crus, the rigidity of the femur fixing means and the crus fixing means in the lengthwise direction is not reduced, thereby providing a foldable knee brace with sufficient rigidity.

It is preferable that the folding portion includes a notch provided on an outer surface of the support portion and extending in the lengthwise direction of the crus.

It is preferable that the folding portion is formed by connecting adjacent band members with a pin.

This configuration makes it possible to provide a foldable rigid knee brace with a simple configuration.

According to the invention as in claim 9, the problem is solved by a knee brace for a knee osteoarthritis patient accompanied by knock-knee including: a femur fixing means to be mounted on a femur of the patient; a crus fixing means to be mounted on a crus of the patient; and an outer leg joint and an inner leg joint respectively fixed to the crus fixing means and the femur fixing means at both ends and arranged on an outer leg side and an inner leg side of a knee joint of the patient for flexing, in which each of the outer leg joint and the inner leg joint include a first coupling means to be arranged along a side of the femur and a second coupling means to be arranged along a side of the crus, the first coupling means and the second coupling means being coupled together by a coupling portion to be arranged at a side of the knee joint, the coupling portion includes a cam groove provided in the first coupling means or the second coupling means, a long groove provided in the second coupling means or the first coupling means, a rotation fulcrum shaft sliding in the long groove and provided to each of the first coupling means or each of the second coupling means, and a cam shaft sliding in the cam groove and provided to the second coupling means or the first coupling means, in which the rotation fulcrum shafts and the cam shafts slide in the long grooves and the cam grooves, respectively, when the patient flexes a knee, and thereby the second coupling means rotate around the coupling portions with respect to the first coupling means to flex the outer leg joint and the inner leg joint, and in which the rotation fulcrum shafts and the cam shafts slide in the long grooves and the cam grooves, respectively, when the outer leg joint and the inner leg joint extend, and thereby the second coupling means on the outer leg side moves downward and rearward and the second coupling means on the inner leg side moves upward and forward.

Due to this configuration, it is possible to provide a knee brace for a knee osteoarthritis patient accompanied by knock-knee.

According to the invention as in claim 10, the problem is solved by a set of an outer leg joint and an inner leg joint of a knee brace for knee osteoarthritis that is fixed to a femur fixing means to be mounted on a femur of a knee osteoarthritis patient and a crus fixing means to be mounted on a crus of the patient at its both ends, that is to be mounted on an outer leg side and an inner leg side of a knee joint of the patient, and that is flexed on side of the knee joint; in which each of the outer leg joint and the inner leg joint include a first coupling means to be arranged along a side of the femur and a second coupling means to be arranged along a side of the crus, the first coupling means and the second coupling means being coupled together by a coupling portion to be arranged at the side of the knee joint, the coupling portion includes a cam groove provided in the first coupling means or the second coupling means, a long groove provided in the second coupling means or the first coupling means, a rotation fulcrum shaft sliding in the long groove and provided to each of the first coupling means or each of the second coupling means, and a cam shaft sliding in the cam groove and provided to the second coupling means or each of the first coupling means, in which the rotation fulcrum shafts and the cam shafts slide in the long grooves and the cam grooves, respectively, when the patient flexes a knee, and thereby the second coupling means rotates around the coupling portions with respect to the first coupling means to flex the outer leg joint and the inner leg joint, and in which the rotation fulcrum shafts and the cam shafts slide in the long grooves and the cam grooves, respectively, when the outer leg joint and the inner leg joint extend, and thereby the second coupling means on the outer leg side moves upward and rearward and the second coupling means on the inner leg side moves downward and forward.

Effect of the Invention

According to the knee brace of the present invention, when the outer leg joint and the inner leg joint extend, by the rotation fulcrum shaft and the cam shaft sliding in the long groove and the cam groove, the second coupling means on the outer leg side moves upward and the second coupling means on the inner leg side moves downward allowing a small space in a site where a knee joint bone should contact to instantly relieve the knee pain when walking, which facilitates the gait training and allows for gradually enhancing the muscles through daily walking. Furthermore, because the knee brace leads to a correct walking trajectory, the gait training can be performed alone without being accompanied by a physical therapist.

Because the body remembers the correct walking trajectory and the muscles are enhanced by continuing the training, the patient can eventually return to the life without pain even if the knee brace is removed.

Moreover, because the coupling portion includes the cam groove provided in each of the first coupling means or each of the second coupling means, the long groove provided in each of the second coupling means or each of the first coupling means, the rotation fulcrum shaft sliding in the long groove and provided to each of the first coupling means or each of the second coupling means, and a cam shaft respectively sliding in the cam groove and provided to each of the second coupling means or each of the first coupling means, and is configured so that, when the patient flexes the knee, the rotation fulcrum shaft and the cam shaft slide in the long groove and the cam groove, respectively, thereby the second coupling means rotates around the coupling portion with respect to the first coupling means to flex the outer leg joint and the inner leg joint, it is not so heavy as the knee brace using the rack and the gear achieving a reduced total weight and enables a smooth and quiet flexion of the leg, which can be worn on the leg without any uncomfortable feeling. Furthermore, by making the cam groove longer, the patient can even sit on heels with the knees flexed further than the right angle while wearing the knee brace according to the present invention.

Moreover, because it is configured so that the second coupling means on the outer leg side moves upward and rearward and the second coupling means on the inner leg side moves downward and forward by the rotation fulcrum shaft and the cam shaft sliding in the long groove and the cam groove, respectively, when the outer leg joint and the inner leg joint extend, the outer leg side of the patient's leg can be pulled upward and the inner leg side can be pulled downward, whereby the knee of the knee osteoarthritis patient with bowleg can be corrected in the direction of raising the flexed leg. Furthermore, because the outer leg side is pulled rearward and the inner leg side is pulled forward when the patient extends the leg, the correction can be performed so as to reproduce the correct screw-home movement.

BRIEF DESCRIPTION OF THE DRAWINGS

FIG. 19 is an illustration showing another exemplary embodiment of the crus support member.

REFERENCE NUMERALS

Figure 1:
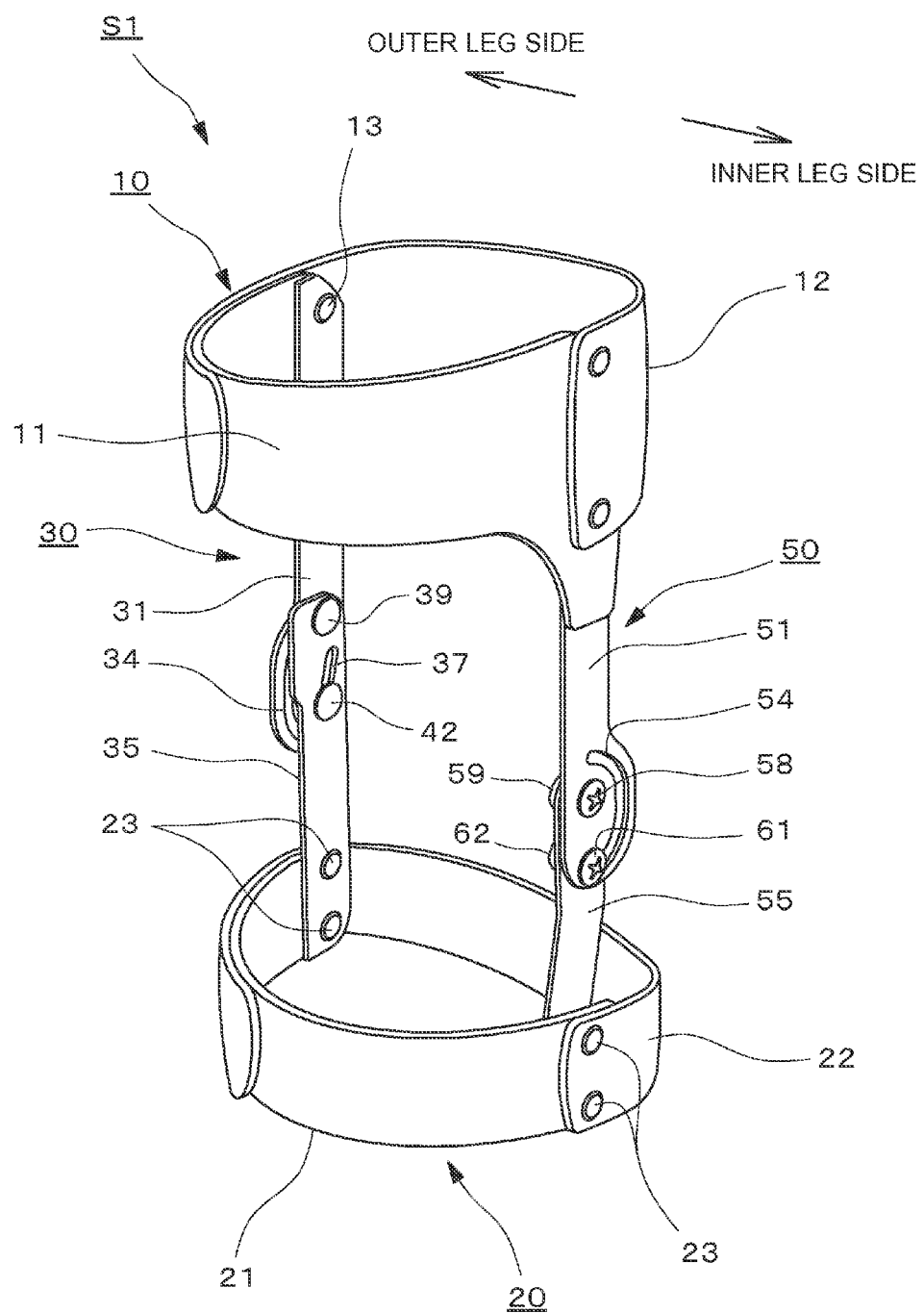
FIG. 1 is a perspective view of a knee brace according to the present invention.

A1 Flexing centerline
A2, A3 Axis
S1, S2, S3 Knee brace
r1, r2, r3, r4, r5, r6 Distance
1 Femur
2 Knee
3 Crus
10, 10' Upper cuff
11, 11' Femur support portion
12, 12' Upper belt
13, 23, 84, 94 Rivet
20, 20' Lower cuff
21, 21' Crus support portion
22, 22' Lower belt
30, 50X Outer leg joint
31, 51X Outer leg upper arm
32, 52 Wide portion
33, 36, 53, 56 Fulcrum shaft hole
33c, 53c Center
33H, 53H Horizontal plane
37', 57' Longitudinal groove
34, 54 Cam groove
34c, 54c Virtual center point
34l, 54l Lower end
34m, 54m Point
34u, 54u Upper end
35, 55X Outer leg lower arm
37, 37X, 57, 57X Inclined groove
38, 41, 58, 61 Check bolt
39, 62 Cam shaft
40, 43, 60, 63 Washer
42, 59 Rotation fulcrum shaft
50, 30X Inner leg joint
51, 31X Inner leg upper arm
55, 35X Inner leg lower arm
55a, 55c Vertical plane
55b Incline plane
11a, 21a Outer leg member
11b, 21b Inner leg member
64, 74 Hinge portion
64a, 64b, 64c Cylinder portion
64d Pin
64e Stopper
65a, 65b, 65c Through hole
66 Concave portion
67a, 67c Spring
68a, 68c Spherical member
69b1, 69b2 Locking groove
69c Attachment
81 Femur support member
83, 93 Notch
85 Cover
86 Covering
87, 88 Strap
87m, 88m Hook-and-loop fastener
91, 91' Crus support member
95 Band member
96 Pin
97 C-shaped portion
98 Convex portion
500 Magnetic pad
501 Covering
502 Magnetic pad body
503 Opening
504 Granular magnet
505 Strap
506 Button
507 Extension
508 Hook-and-loop fastener

DETAILED DESCRIPTION OF THE INVENTION

Hereinbelow, embodiments of the present invention will be described with reference to drawings. It should be noted that members, arrangements, and the like described below do not limit the present invention in any ways but naturally can be altered in various ways without departing from the scope of the present invention.

A knee brace S1 according to this embodiment is a brace to be worn around a knee 2 of a knee osteoarthritis patient, generally including, as shown in FIG. 1, an upper cuff 10 as a femur fixing means wound around a femur 1, a lower cuff 20 as a crus fixing means wound around a crus 3, and an outer leg joint 30 and an inner leg joint 50 fixed to the upper cuff 10 and the lower cuff 20 at both ends and arranged on either side of a site peripheral to the knee joint of the patient. FIG. 1 depicts the knee brace S1 for a right leg of a bowleg patient.

The upper cuff 10 includes a substantially cylindrical femur support portion 11 made from a rigid material and an upper belt 12 fixed to one end side of the femur support portion 11 in a lateral direction. The femur support portion 11 is in a substantially cylindrical shape curved around a front side of the femur 1 of the patient. The upper belt 12 has a strap including a fixing means such as a button and a hook-and-loop fastener on its free end side, and is configured to support a rear side of the femur 1 of the patient by fixing the strap of the upper belt 12 to the femur support portion 11 using the fixing means.

The lower cuff 20 includes a substantially cylindrical crus support portion 21 made from a rigid material and a lower belt 22 fixed to one end side of the crus support portion 21 in the lateral direction. The crus support portion 21 is in a substantially cylindrical shape curved around a front side of the crus 3 of the patient. The lower belt 22 has a strap including a fixing means such as a button and a hook-and-loop fastener on its free end side, and is configured to support a rear side of the crus 3 of the patient by fixing the strap of the lower belt 22 to the crus support portion 21 using the fixing means.

The crus support portion 21 of the lower cuff 20 is formed by a material more rigid than that of the femur support portion 11 of the upper cuff 10.

Figure 2:
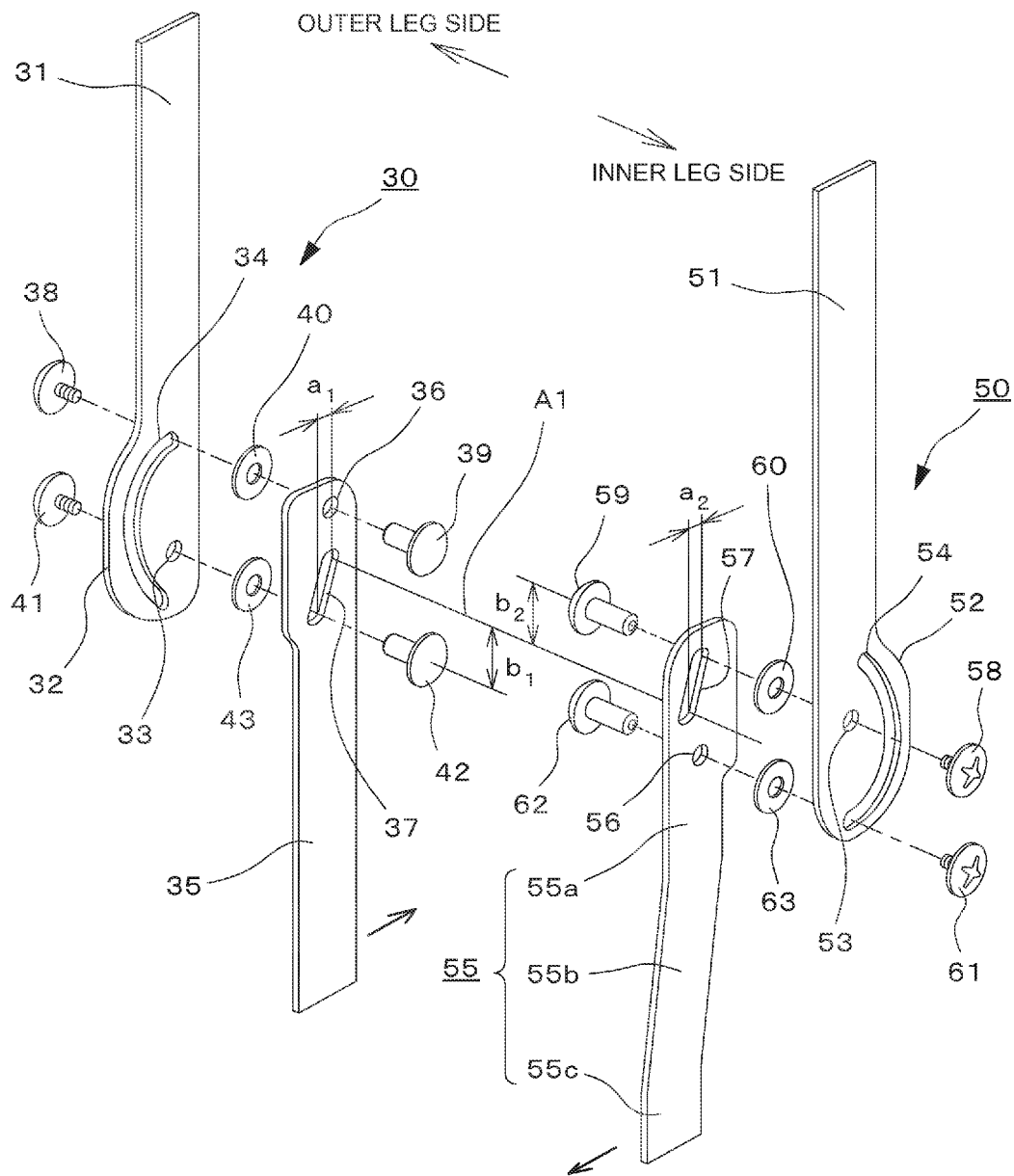
FIG. 2 is an exploded view of a set of an outer leg joint and an inner leg joint according to an embodiment of the present invention.

The outer leg joint 30 includes, as shown in FIG. 2, an outer leg upper arm 31 as a first coupling means and an outer leg lower arm 35 as a second coupling means. The outer leg upper arm 31 and the an outer leg upper arm 31 as a first coupling means and an outer leg lower arm 35 are made from a rigid material containing a mixture of about 70 wt % plastic and about 30 wt % carbon.

The outer leg upper arm 31 includes a substantially tabular body including a wide portion 32 formed slightly wider on its lower end side. The wide portion 32 is provided with a fulcrum shaft hole 33 and a cam groove 34 in a substantially arc shape so as to surround one end side of the fulcrum shaft hole 33.

Figure 3:
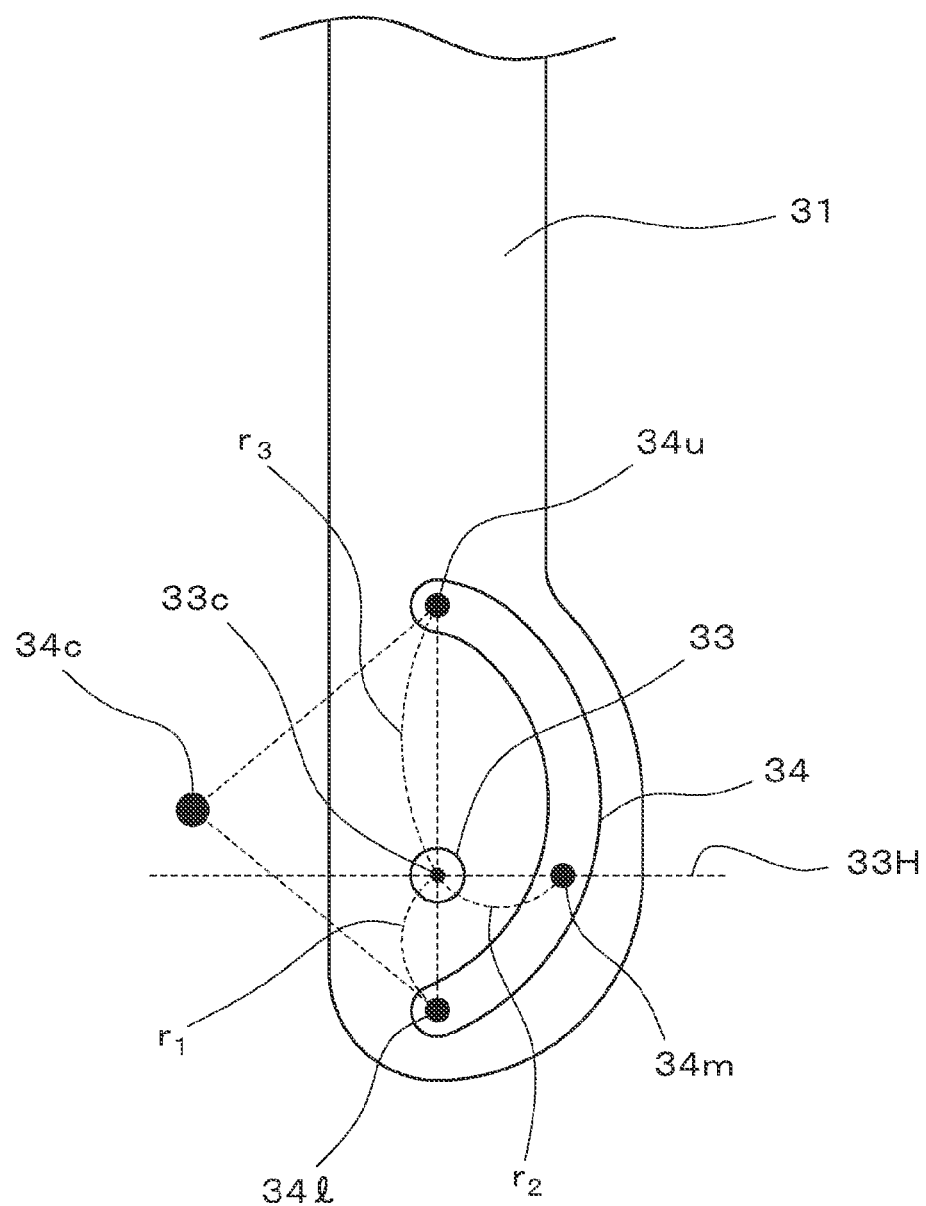
FIG. 3 is an illustration of an outer leg upper arm according to an embodiment of the present invention.

The cam groove 34 is formed in a substantially arc shape centered at a virtual center point 34c, as shown in FIG. 3. The fulcrum shaft hole 33 is included inside a sector shape formed by the cam groove 34 and the virtual center point 34c of the cam groove 34.

A lower end 34l in FIG. 3 is where a center of a cam shaft 39 is located when the cam shaft 39 comes to the lower end of the cam groove 34. An upper end 34u is where the center of the cam shaft 39 is located when the cam shaft 39 comes to the upper end of the cam groove 34. A point 34m is a point at which a horizontal plane 33H including a center 33c of the fulcrum shaft hole 33 crosses a centerline of the cam groove 34 and at which the cam shaft 39 is located when the patient flexes the knee to the right angle. An angle between a line connecting the upper end 34u to the center 33c and a line connecting the point 34m to the center 33c is, as shown in FIG. 3, substantially right.

The fulcrum shaft hole 33 is provided closer to the lower end 34l than the upper end 34u.

A distance between the fulcrum shaft hole 33 and the cam groove 34 is formed to increase upward from the lower end 34l of the cam groove 34.

A distance r1 from the lower end 34l to the center 33c of the fulcrum shaft hole 33 is substantially same as a distance r2 from the point 34m to the center 33c. A distance r3 from the upper end 34u to the center 33c is made larger than r1 and r2, satisfying $r1 \cong r2 < r3$. The point 34m is the point at which the cam shaft 39 is located when the patient flexes the knee to the right angle, and, with the outer leg joint 30, the cam shaft 39 and a rotation fulcrum shaft 42 line up on the horizontal plane 33H in the state where the patient is flexing the knee to the right angle.

The outer leg lower arm 35 includes a substantially tabular body with a relatively wider upper end. Formed near the upper end of the outer leg lower arm 35 is a fulcrum shaft hole 36, and formed below the fulcrum shaft hole 36 is an inclined groove 37 as a straight long groove. The inclined groove 37 is formed to incline at a predetermined angle, such as 20-30 degrees, with respect to a lengthwise direction of the outer leg lower arm 35.

The inclined groove 37 in the outer leg lower arm 35 is formed with its lower end side inclined forward to the crus 3. Thus, by displacing the knee flexed to the right angle as shown in FIG. 9(A)(O) to the state of the knee extended as shown in FIG. 9(C)(O), the outer leg lower arm 35 moves rearward to the patient to pull the outer leg side of the crus 3 rearward via a portion of the lower cuff 20 on the outer leg side.

The cam shaft 39 is inserted in the cam groove 34 and the fulcrum shaft hole 36 from the fulcrum shaft hole 36 side to engage with a check bolt 38 inserted from the cam groove 34 side. A washer 40 is put around the cam shaft 39 and the check bolt 38 between the cam groove 34 and the fulcrum shaft hole 36.

The rotation fulcrum shaft 42 is inserted in the fulcrum shaft hole 33 and the inclined groove 37 from the inclined groove 37 side to engage with a check bolt 41 inserted from the fulcrum shaft hole 33 side. A washer 43 is put around the rotation fulcrum shaft 42 and the check bolt 41 between the fulcrum shaft hole 33 and the inclined groove 37.

Although the cam shaft 39 and the rotation fulcrum shaft 42 are inserted in the fulcrum shaft hole 36 and the cam groove 34, and in the fulcrum shaft hole 33 and the inclined groove 37 according to this embodiment, the present invention is not limited to this configuration but may be configured so that, for example, a protrusion projecting from a position where the fulcrum shaft holes 36, 33 are provided are formed instead of the fulcrum shaft holes 36, 33, the cam shaft 39, and the rotation fulcrum shaft 42, and that these protrusions slide respectively in the cam groove 34 and the inclined groove 37.

The inner leg joint 50 includes, as shown in FIG. 2, an inner leg upper arm 51 as the first coupling means and an inner leg lower arm 55 as the second coupling means. The inner leg upper arm 51 and the inner leg lower arm 55 are made from a rigid material containing a mixture of about 70 wt % plastic and about 30 wt % carbon.

The inner leg upper arm 51 includes a substantially tabular body including a wide portion 52 formed slightly wider on its lower end side.

The wide portion 52 is provided with a fulcrum shaft hole 53 and a cam groove 54 in a substantially arc shape so as to surround one end side of the fulcrum shaft hole 53.

Figure 4:
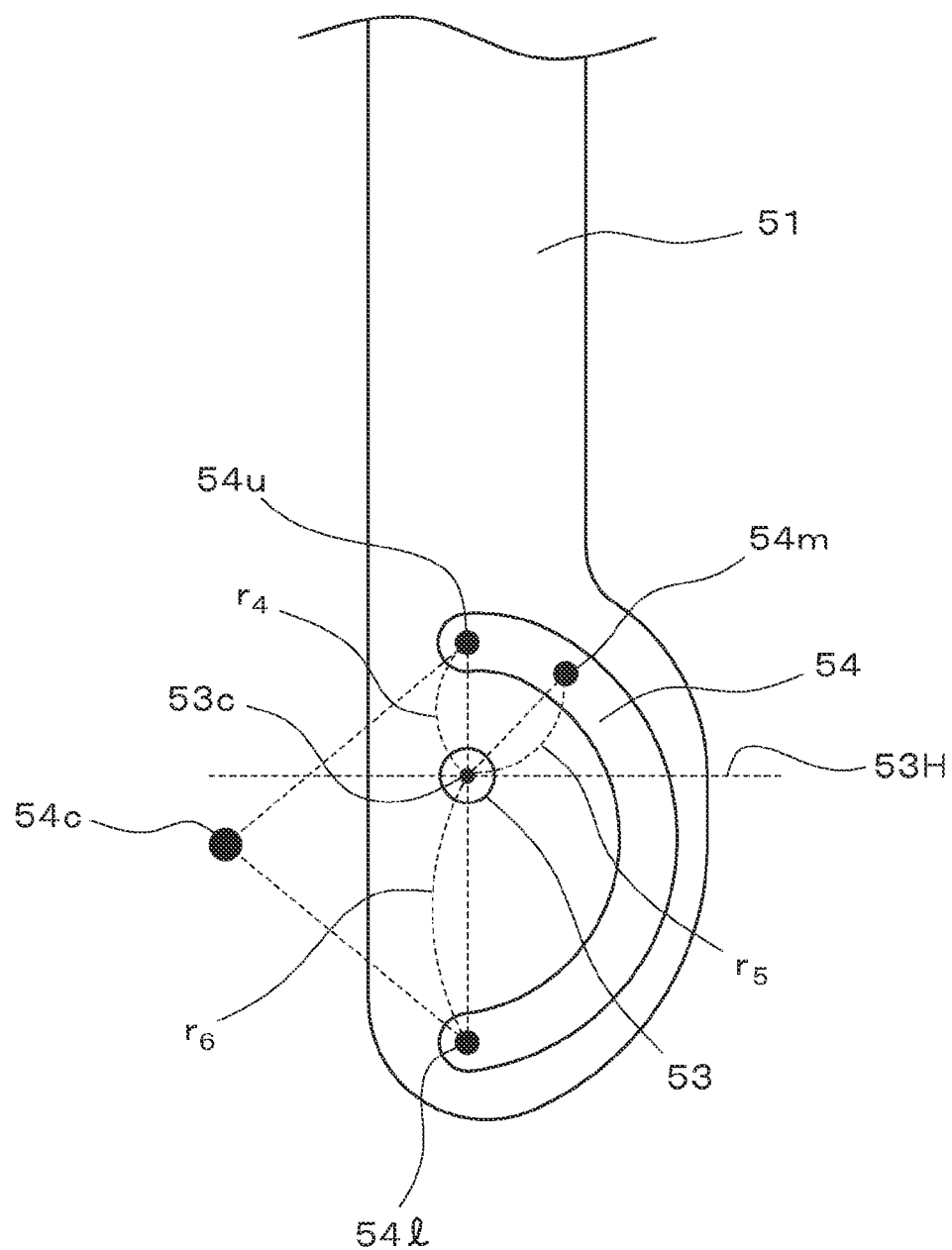
FIG. 4 is an illustration of an inner leg upper arm according to an embodiment of the present invention.

The cam groove 54 is formed in a substantially arc shape centered at a virtual center point 54c, as shown in FIG. 4. The fulcrum shaft hole 53 is included inside a sector shape formed by the cam groove 54 and the virtual center point 54c of the cam groove 54.

A lower end 54l is where a center of a cam shaft 62 is located when the cam shaft 62 comes to the lower end of the cam groove 54. An upper end 54u is where the center of the cam shaft 62 is located when the cam shaft 62 comes to the upper end of the cam groove 54.

A point 54m is a point on a centerline of the cam groove present between a point at which a horizontal plane 53H including a center 53c of the fulcrum shaft hole 53 crosses a centerline of the cam groove 54 and the upper end 54u. The 54m is a point at which the cam shaft 62 is located when the patient flexes the knee to the right angle. An angle between a line connecting the upper end 54u to the center 53c and a line connecting the point 54m to the center 53c is a sharp angle of about 60-70 degrees.

The fulcrum shaft hole 53 is provided closer to the upper end 54u than the lower end 54l.

A distance between the fulcrum shaft hole 53 and the cam groove 54 is formed to increase downward.

A distance r4 from the upper end 54u to the center 53c of the fulcrum shaft hole 53 is substantially same as a distance r5 from the point 54 to the center 53c. A distance r6 from the lower end 54l to the center 53c is made larger than r4 and r5, satisfying $r4 \cong r5 < r6$. The point 54m is the point at which a rotation fulcrum shaft 59 is located when the patient flexes the knee to the right angle, and, with the inner leg joint 50, the cam shaft 62 is located obliquely upward of the rotation fulcrum shaft 59 in the state where the patient is flexing the knee to the right angle.

Figure 13:
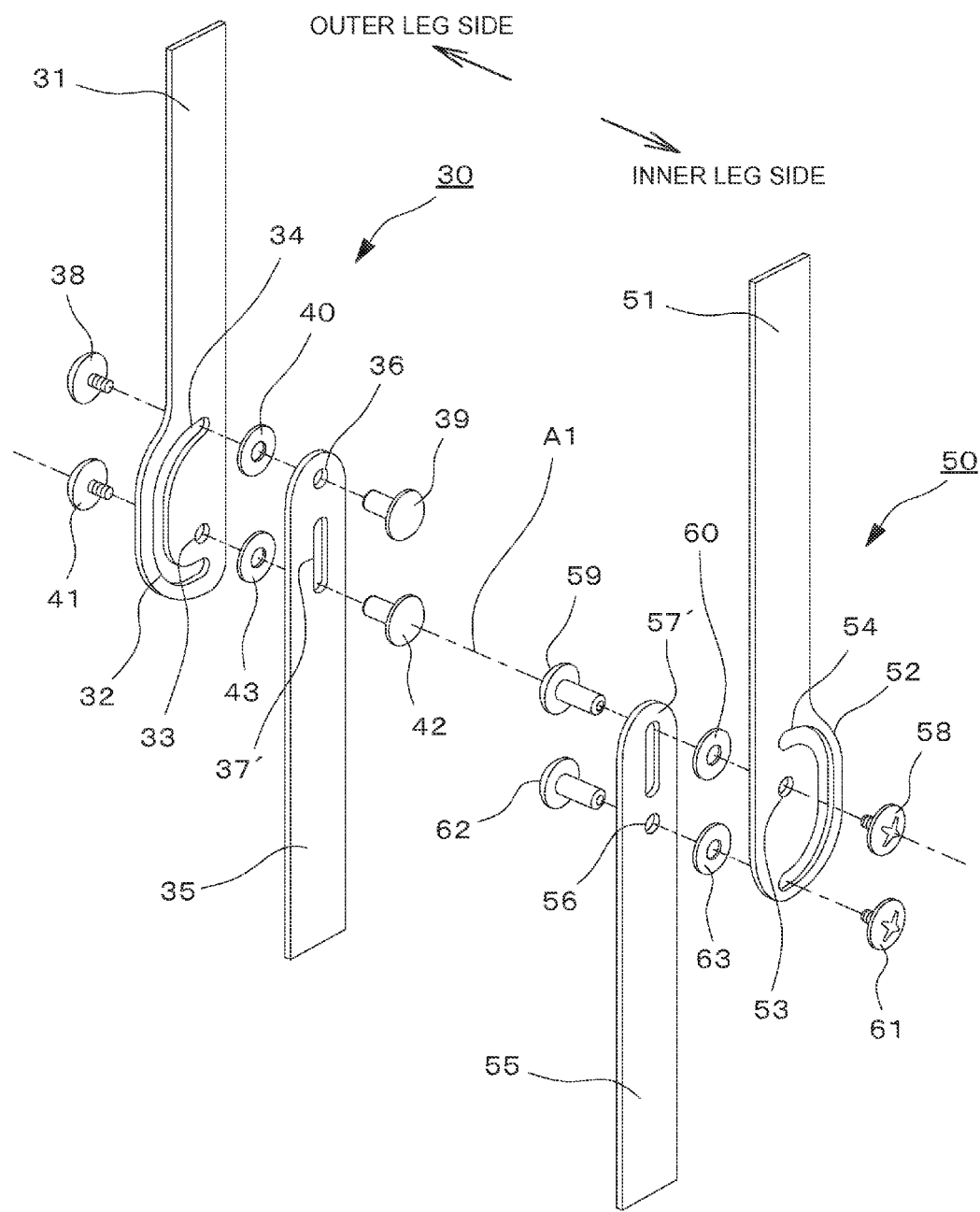
FIG. 13 is an illustration showing an exemplary set of the outer leg joint and the inner leg joint.

Although the cam grooves 34, 54 are formed substantially on an arc, the cam groove 34 may be formed with its curvature increasing downward and the cam groove 54 may be formed with its curvature increasing upward, as shown in FIG. 13. Such a configuration can achieve the two formulae r1≅r2<r3 and r4≅r5<r6.

The cam groove 34 on a side of which total length shrinks when the outer leg joint 30 and the inner leg joint 50 are extended, i.e. the outer leg side according to this embodiment, has a curved shape convex forward, and a side of which total length extends, i.e. the cam groove 54 on the inner leg side, has a curved shape convex rearward.

The inner leg lower arm 55 includes a substantially tabular body with a relatively wider upper end. The inner leg lower arm 55 includes, as shown in FIG. 2, a vertical plane 55a coupled with the inner leg upper arm 51 to be substantially vertical when attached to the patient's leg, an inclined plane 55b continuing from the vertical plane 55a and inclined to be closer to the leg side with an angle of about 10-15 degrees with respect to the vertical plane 55a, and a vertical plane 55c continuing from the inclined plane 55b and parallel with the vertical plane 55a. With this configuration, the inner leg joint 50 can fit the patient's leg better.

On the vertical plane 55a of the inner leg lower arm 55, a straight inclined groove 57 is formed near the upper end as the long groove, and a fulcrum shaft hole 56 is formed below the inclined groove 57. The inclined groove 57 is formed to incline at a predetermined angle, such as 20-30 degrees, with respect to a lengthwise direction of the outer leg lower arm 55.

The inclined groove 57 is formed with its upper end side inclined rearward to the crus 3. Thus, by displacing the knee flexed to the right angle as shown in FIG. 9(A)(I) to the state of the knee extended as shown in FIG. 9(C)(I), the inner leg lower arm 55 moves to the front side of the patient to pull the inner leg side of the crus 3 forward via a portion of the lower cuff 20 on the inner leg side.

The inclined groove 57 is not limited to the straight shape but may be formed in a curved shape slightly convex toward an obliquely downward direction. Although the side on which the joint contracts receives a higher resistance than the side on which the joint extends, the inclined groove 57 can smooth the movement of the rotation fulcrum shaft 59 on the inner leg side that receives the higher resistance when flexing the knee because a moving distance of the rotation fulcrum shaft 59 is longer than that of the rotation fulcrum shaft 42.

The cam shaft 62 is inserted in the cam groove 54 and the fulcrum shaft hole 56 from the fulcrum shaft hole 56 side to engage with a check bolt 61 inserted from the cam groove 54 side. A washer 63 is put around the cam shaft 62 and the check bolt 61 between the cam groove 54 and the fulcrum shaft hole 56.

The rotation fulcrum shaft 59 is inserted in the fulcrum shaft hole 53 and the inclined groove 57 from the inclined groove 47 side to engage with a check bolt 58 inserted from the fulcrum shaft hole 53 side. A washer 60 is put around the rotation fulcrum shaft 59 and the check bolt 58 between the fulcrum shaft hole 53 and the inclined groove 57.

A distance from the upper end 54u to the lower end 54l of the cam groove 54 is made shorter than a distance from the upper end 34u to the lower end 34l of the cam groove 34 by approximately 10-20%.

The outer leg joint 30 is, as shown in FIG. 1, fixed to the upper cuff 10 and the lower cuff 20 by the upper end side of the outer leg upper arm 31 being fixed to a side inner surface of the upper cuff 10 on the outer leg side with a rivet 13 and by the lower end side of the outer leg lower arm 35 being fixed to the side inner surface of the lower cuff 20 on the outer leg side with a rivet 23.

The inner leg joint 50 is, as shown in FIG. 1, fixed to the upper cuff 10 and the lower cuff 20 by the upper end side of the inner leg upper arm 51 being fixed to the side inner surface of the upper cuff 10 on the inner leg side with an unshown rivet and by the lower end side of the inner leg lower arm 55 being fixed to the side inner surface of the lower cuff 20 on the inner leg side with the rivet 23.

Next, an operation and an action of the knee brace S1 according to this embodiment will be described.

Figure 9:
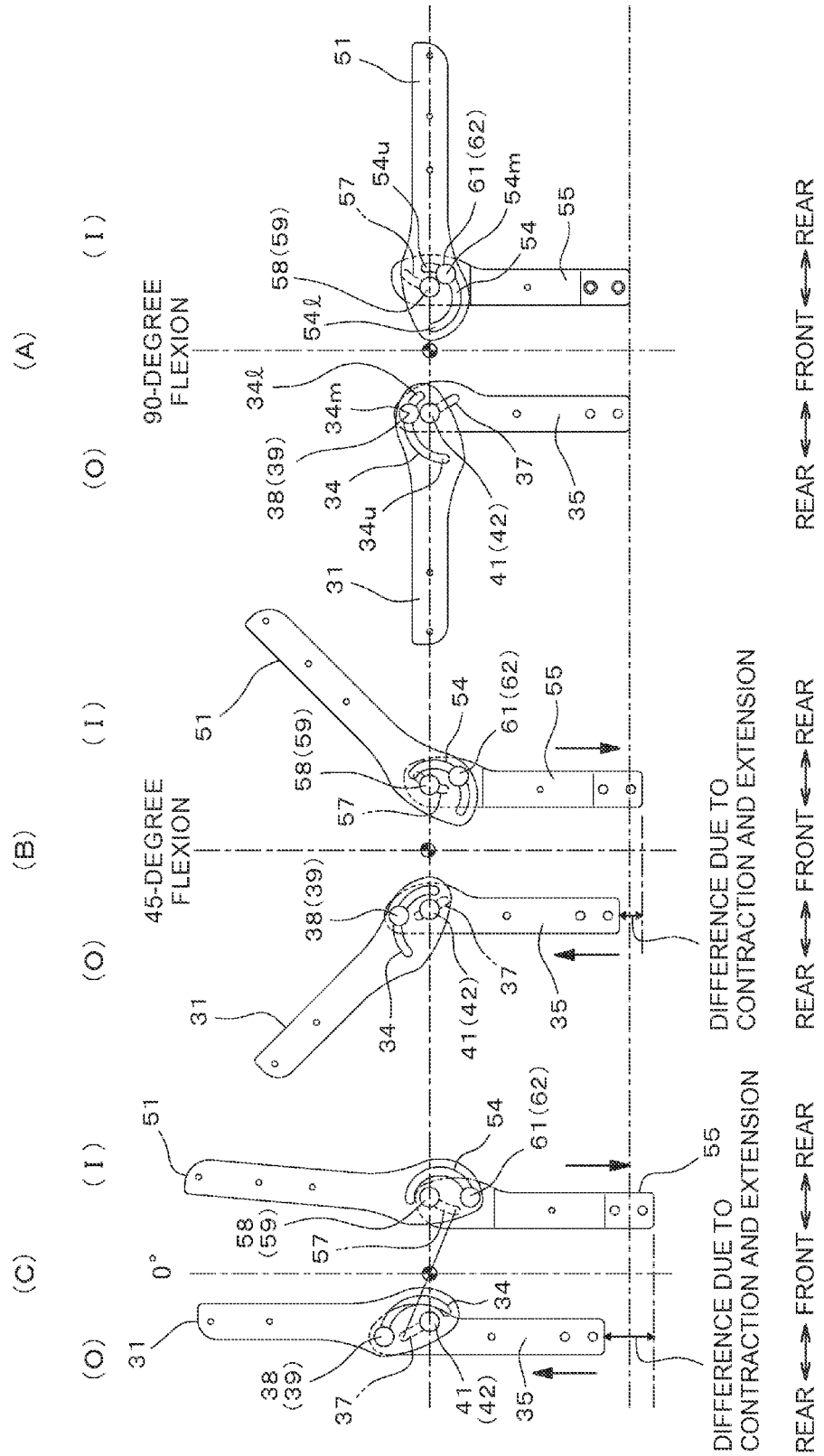
FIG. 9 is an illustration of states in which the set of the outer leg joint and the inner leg joint according to an embodiment of the present invention is flexed to the right angle, to 45 degrees, and extended state.
Figure 10:
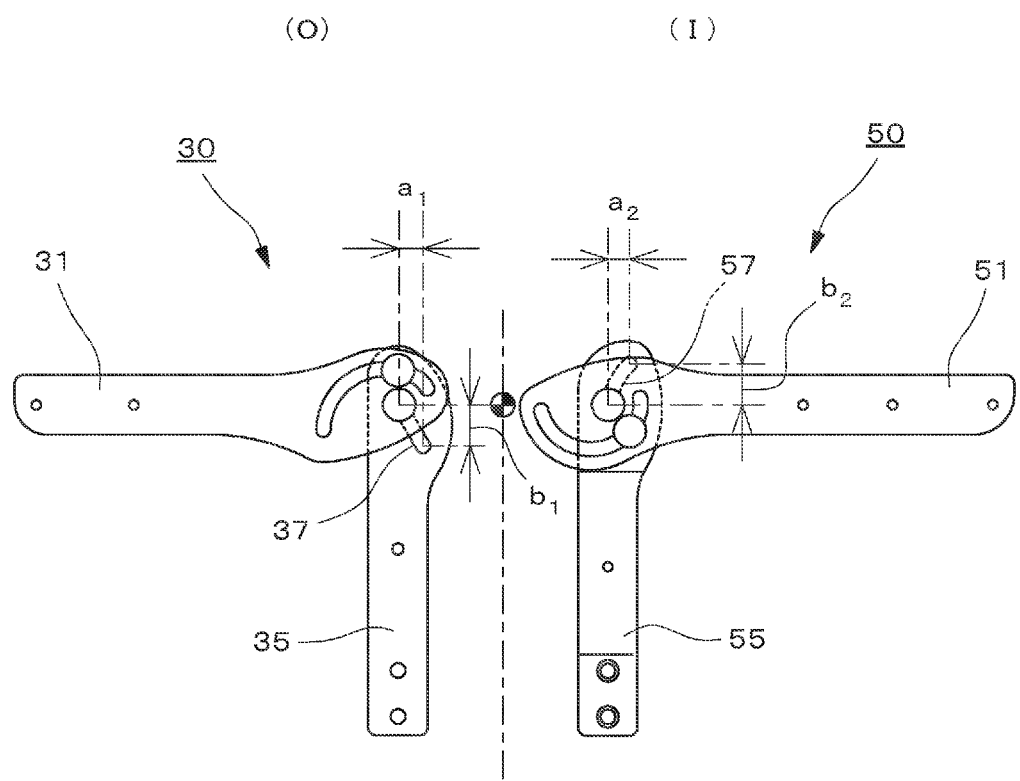
FIG. 10 is an illustration showing an extensible distance of the outer leg joint and the inner leg joint according to an embodiment of the present invention.

Operations of the cam shafts 39, 62 and the rotation fulcrum shafts 42, 59 will be described first with reference to FIG. 9. It should be noted that the outer leg upper arm 51 and the inner leg upper arm 31 in FIGS. 9 and 10 represent slightly different shapes of the wide portions 52, 32, respectively.

In a process of the patient relaxing the knee joint from the most flexed state such as sitting on heels to the state of flexing the knees to the right angle, as shown in FIG. 9(A)(O), the cam shaft 39 moves from the lower end 34l to the point 34m in the cam groove 34. At this time, because r1 and r2 shown in FIG. 3 are of the substantially same length, the rotation fulcrum shaft 42 does not move in the inclined groove 37 and stays at the upper end of the inclined groove 37.

In a process of the patient extending the knee joint from the right angle, as shown in FIG. 9(C)(O), the cam shaft 39 moves from the point 34m toward the upper end 34u in the cam groove 34. At this time, because the distance from the center 33c to the cam groove 34 in FIG. 3 gradually increases from the point 34m toward the upper end 34u, the rotation fulcrum shaft 42 is pushed in the inclined groove 37 to move toward the lower end.

Accordingly, in the state of sitting on heels or on a chair where the flexion angle of the knee is 90 degrees or larger, the knee joint is not applied with a force to pull or compress the crus 3 in an up and down and front to back direction. On the contrary, in the state of walking or standing where the flexion angle of the knee is 90 degrees or smaller, the cam shaft 39 moves toward the lower end in the inclined groove 37 thereby applying a force to pull the crus 3 upward and rearward.

In the process of the patient extending the knee joint from the most flexed state such as sitting on heels to the state of flexing the knees to the right angle, as shown in FIG. 9(A)(I), the cam shaft 62 moves, in the cam groove 54, from the upper end 54u to the point 54m shown in FIG. 4. At this time, because r4 and r5 shown in FIG. 4 are of the substantially same length, the rotation fulcrum shaft 59 does not move in the inclined groove 57 and stays at the lower end of the inclined groove 57.

In the process of the patient extending the knee joint from the right angle, as shown in FIG. 9(A)(I), the cam shaft 62 moves from the point 54m toward the lower end 54l in the cam groove 54. At this time, because the distance from the center 53c to the cam groove 54 in FIG. 4 gradually increases toward the point 54m toward the lower end 54l, the rotation fulcrum shaft 59 is pushed in the inclined groove 57 to move toward the upper end.

Accordingly, in the state with the flexion angle of the knee being 90 degrees or larger, the knee joint is not applied with a force to pull or compress the crus 3 in the up and down and front to back direction. On the contrary, in the state with the flexion angle of the knee being 90 degrees or smaller, the rotation fulcrum shaft 59 moves toward the upper end in the inclined groove 57, thereby applying a force to pull the crus 3 downward and forward.

Figure 5:
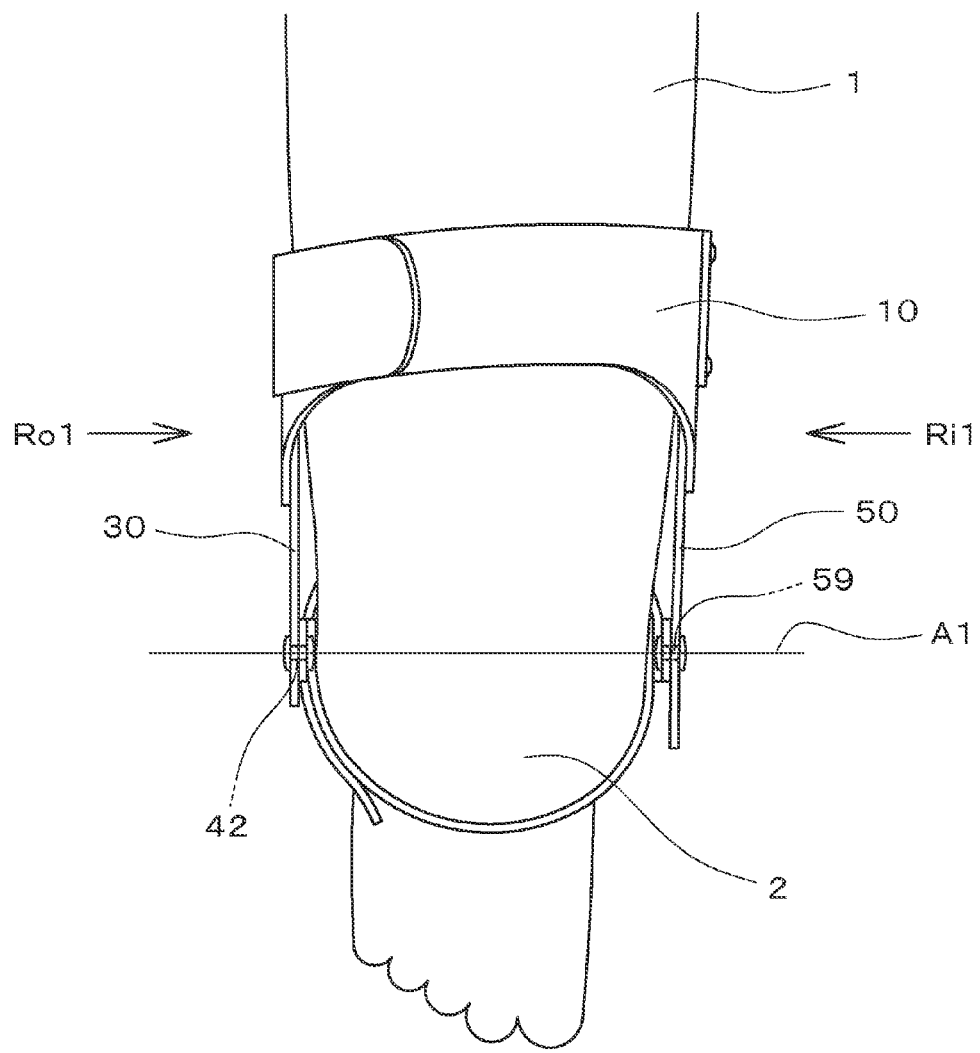
FIG. 5 is an illustration of a state where a patient wearing the knee brace according to an embodiment of the present invention is flexing the knee to the right angle.
Figure 6:
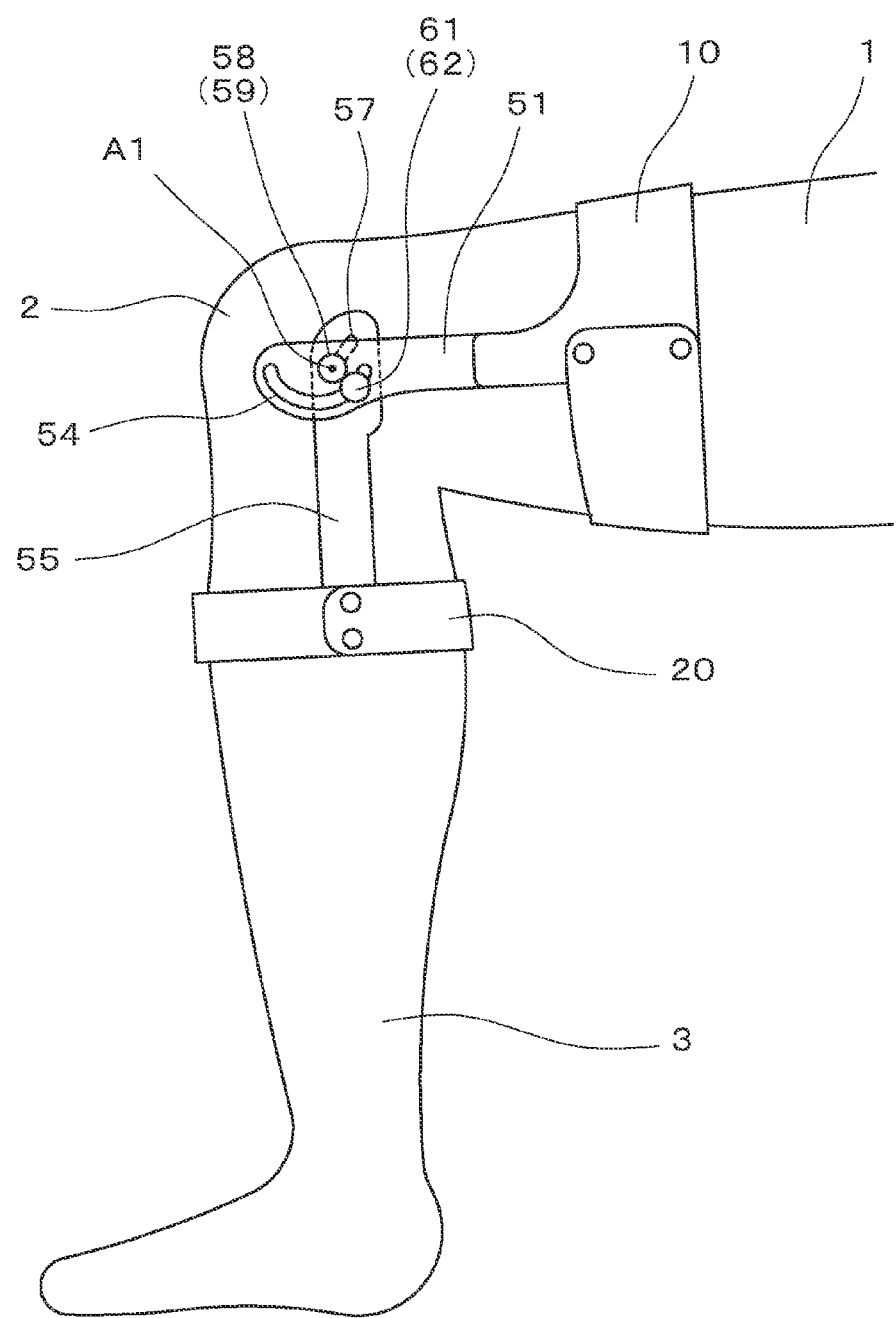
FIG. 6 is an illustration of a state where the patient wearing the knee brace according to an embodiment of the present invention is flexing the knee to the right angle.

The knee brace S1 according to this embodiment takes the state where the patient flexes the knee 2 to the right angle as shown in FIGS. 5 and 6 as the reference position. The knee brace S1 is worn so that, in the reference position, the rotation fulcrum shaft 42 and the rotation fulcrum shaft 59 on the same flexing centerline A1 and that the flexing centerline A1 coincides with an axis of the flexion movement of the knee joint of the patient. At this time, as shown in FIGS. 6 and 9(A)(I), the rotation fulcrum shaft 59 on the inner leg side is located substantially at the lower end of the inclined groove 57, and the cam shaft 62 is located at about a quarter from the upper end 54u on the upper side of the femur 1 in the cam groove 54.

Figure 7:
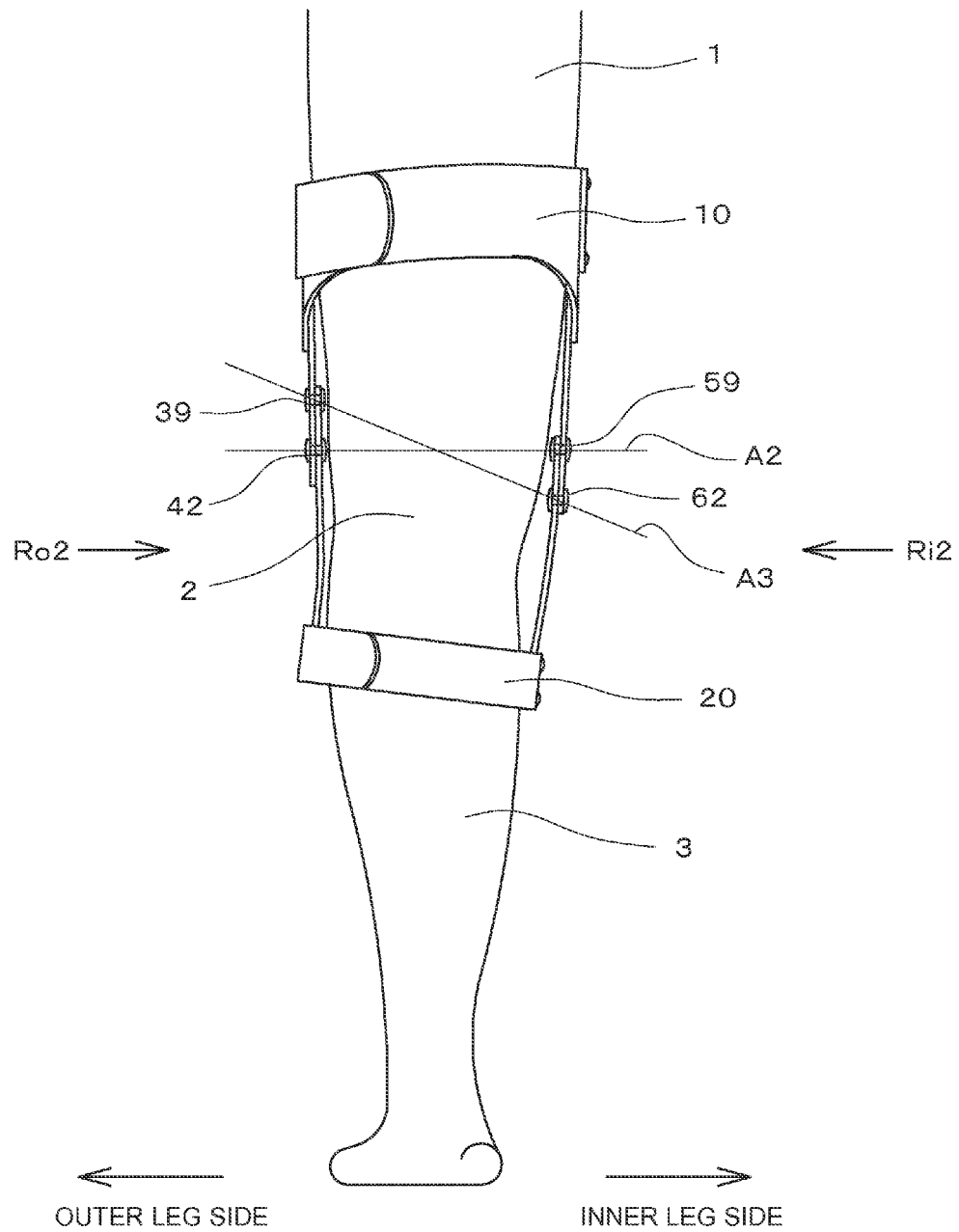
FIG. 7 is an illustration of a state where the patient wearing the knee brace according to an embodiment of the present invention is extending the knee.
Figure 8:
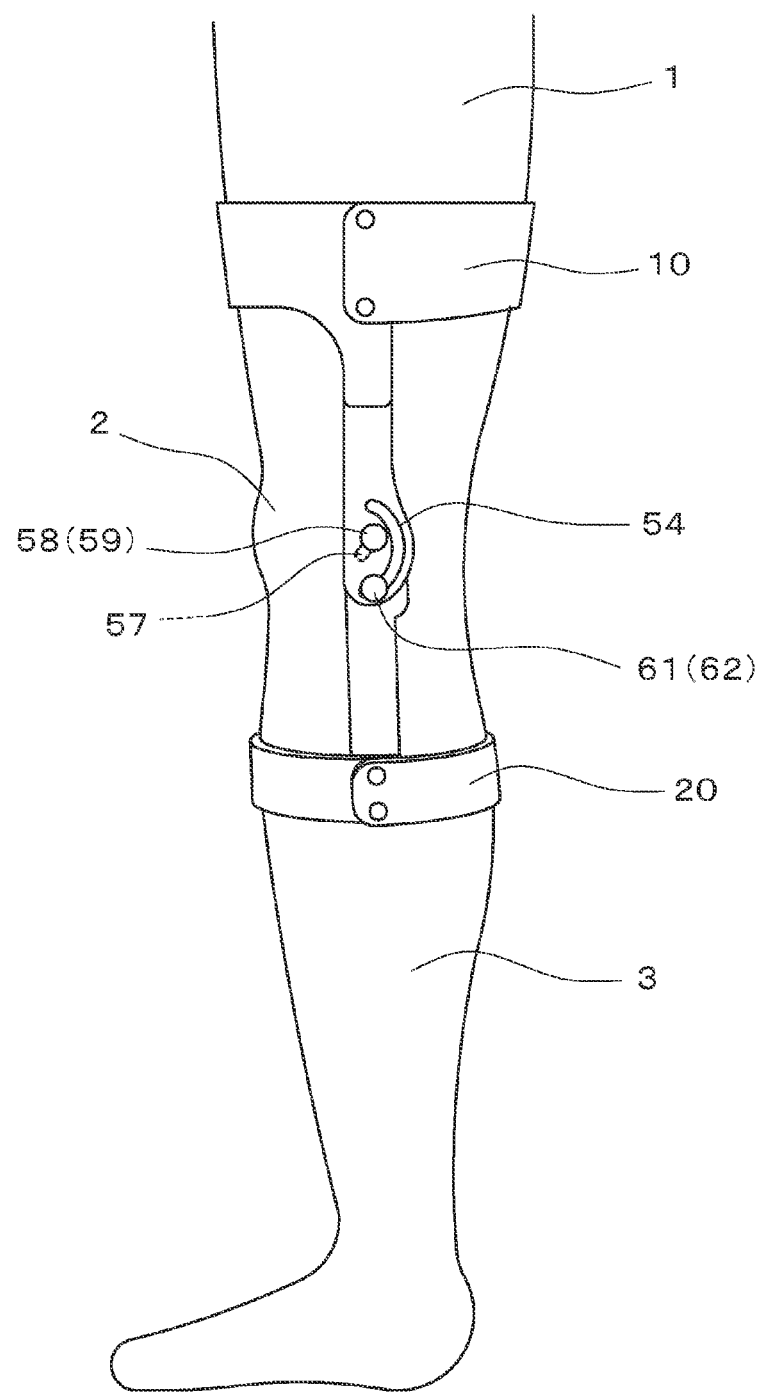
FIG. 8 is an illustration of a state where the patient wearing the knee brace according to an embodiment of the present invention is extending the knee.

In the state where the patient extends the knee 2, as shown in FIGS. 8 and 9(A)(I), the rotation fulcrum shaft 59 on the inner leg side is located at the upper end of the inclined groove 57, and the cam shaft 62 is located at the lower end of the cam groove 54. Furthermore, as shown in FIG. 9(C)(O), the rotation fulcrum shaft 42 is located at the lower end of the inclined groove 37, and the cam shaft 39 is located at the upper end of the cam groove 34. As shown in FIG. 7, an axis connecting the rotation fulcrum shaft 42 to the rotation fulcrum shaft 59 is an axis A2, and an axis connecting the cam shaft 39 to the cam shaft 62 is an axis A3 inclined so that the inner leg side is lower.

Next, an explanation about the operation of the knee brace S1 shown in FIGS. 5 to 8 associated with change in vertical lengths of the outer leg joint 30 and the inner leg joint 50 will be given focusing on both joints 30 and 50.

FIG. 9(A)(O) is a view of the outer leg joint 30 in FIG. 5 from an arrow Ro1, FIG. 9(A)(I) is a view of the inner leg joint 50 in FIG. 5 on an arrow Ri1, FIG. 9(C)(O) is a view of the outer leg joint 30 in FIG. 7 on an arrow Ro2, and FIG. 9(C)(I) is a view of the inner leg joint 50 in FIG. 7 on an arrow Ri2.

In the reference position where the knee joint is flexed to the right angle, as shown in FIGS. 5 and 6, the rotation fulcrum shaft 42 and the rotation fulcrum shaft 59 are on the same substantially horizontal flexing centerline A1, the outer leg lower arm 35 and he inner leg lower arm 55 are substantially horizontal, and a correction force is not applied to the patient's knee in the vertical direction. At this time, the outer leg lower arm 35 and the inner leg lower arm 55 are arranged at the same height along the flexing centerline A1, and the outer leg joint 30 and the inner leg joint 50 are both flexing to the right angle.

In the state where the patient is extending the knee joint, as shown in FIGS. 7, 8, and 9(C), the cam shaft 62 moves to the lower end 54l of the cam groove 54 in FIG. 4, and the cam shaft 39 moves to the upper end 34u of the cam groove 34 in FIG. 4. Thus, as shown in FIGS. 9(C)(O) and (I), the outer leg lower arm 35 is raised by the cam shaft 39 and the inner leg lower arm 55 is pushed down by the cam shaft 62, and the lower end of the outer leg lower arm 35 is located higher than the lower end of the inner leg lower arm 55 by the difference due to contraction and extension.

The extensible distance of the outer leg joint 30 and the inner leg joint 50 in the up and down and front to back direction will be described with reference to FIG. 10.

The distance by which the outer leg joint 30 contracts is substantially equal to a length component b1 of the inclined groove 37 in the lengthwise direction of the outer leg lower arm 35. The distance by which the outer leg joint 30 is pulled rearward is substantially equal to a length component a1 of the inclined groove 37 in the lengthwise direction of the outer leg lower arm 35.

The distance by which the inner leg joint 50 extends is substantially equal to the length component b2 of the inclined groove 57 in the lengthwise direction of the inner leg lower arm 55. The distance by which the inner leg joint 50 is pulled forward is substantially equal to the length component a2 of the inclined groove 57 in the lengthwise direction of the inner leg lower arm 55.

Thus, in the state where the knee brace S1 is extended, there is a difference due to contraction and extension b1+b2 in the vertical direction between the outer leg joint 30 and the inner leg joint 50.

Moreover, in the state where the knee brace S1 is extended, there is a displacement a1+a2 in the front to back direction between the outer leg joint 30 and the inner leg joint 50, which displacement causes a twist to reproduce the screw-home movement.

Figure 11:
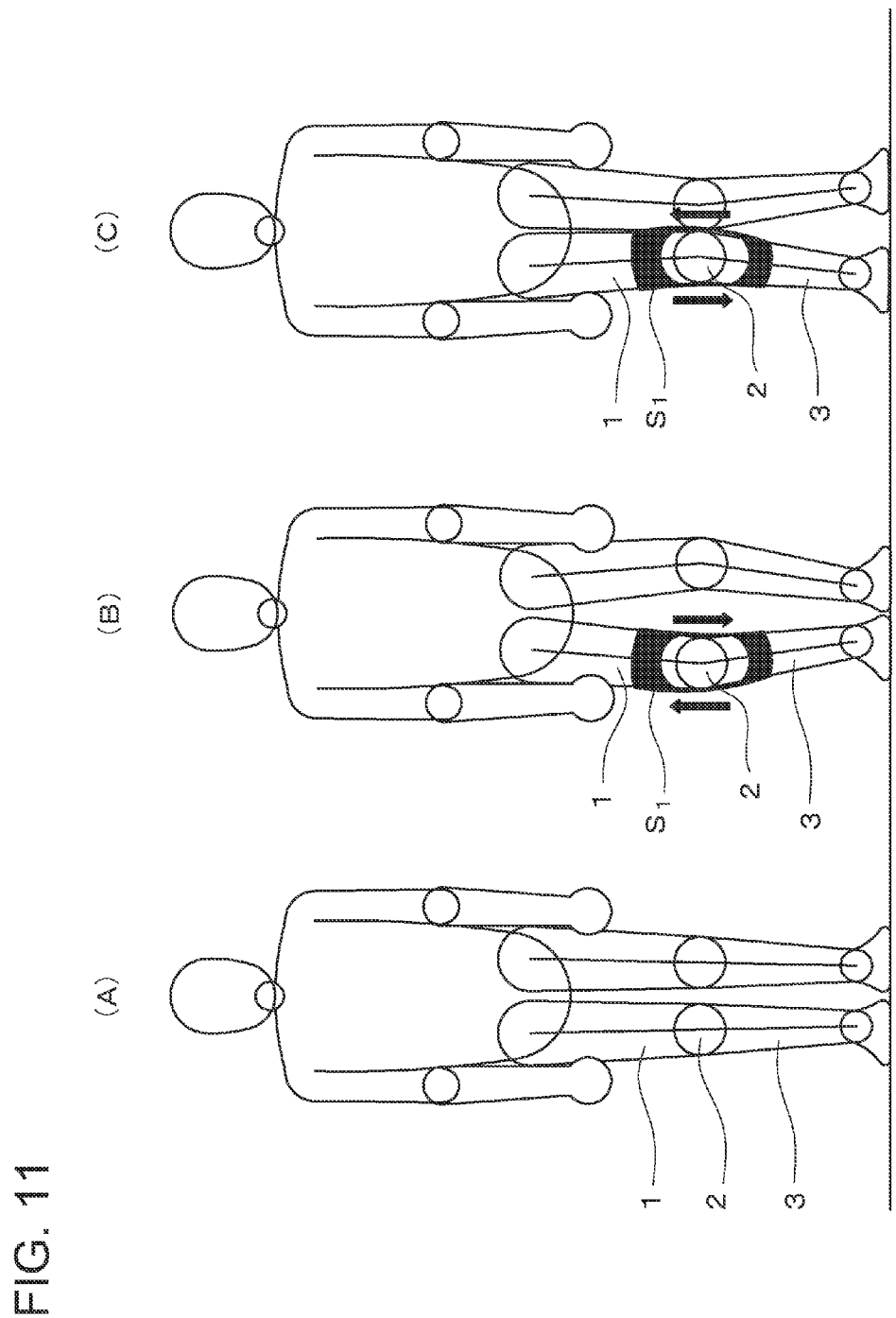
FIG. 11 is an illustration showing a corrective force applied when wearing the knee brace according to an embodiment of the present invention.

In this embodiment, in the state where the patient is extending the knee joint, as shown in FIG. 11(B), the outer leg side of the crus 3 of the knee osteoarthritis patient accompanied by bowleg is pulled up and the inner leg side is pushed down. This can correct the bowleg in a direction of returning the bowleg to the correct state of the knee as shown in FIG. 11(A).

Furthermore, because the knee osteoarthritis patient with bowleg often has the cartilage on the inner leg side of the knee joint being worn and feels pain due to direct contact between bones, a space can be formed between the upper and lower bones of the knee joint on the inner leg side by pushing down the inner leg side of the crus 3, thereby reducing the pain due to the contact between the bones.

Although this embodiment is configured to move the outer leg lower arm 35 upward and the inner leg lower arm 55 downward when extended, the invention is not limited to this configuration but may be configured not to move one of the outer leg lower arm 35 and the inner leg lower arm 55 in the vertical direction but to move only the other one upward or downward by forming one of the inclined grooves 37, 57 as a shaft hole that is not elongated.

Because the inclined groove 37 in the outer leg lower arm 35 is formed with its lower end side inclined on the front side of the crus 3, when the knee is displaced from the state of flexing to the right angle as shown in FIG. 9(A)(O) to the extended state shown in FIG. 9(C)(O), the outer leg lower arm 35 moves to the front side of the patient and pulls the outer leg side of the crus 3 rearward via a portion on the outer leg side of the lower cuff 20.

Thus, when the patient extends the knee from the flexed state, the outer leg lower arm 35 moves rearward as shown in FIG. 9(C)(O) to pull the portion on the outer leg side of the lower cuff 20 rearward and the inner leg lower arm 55 moves forward as shown in FIG. 9(C)(I) to pull the portion on the inner leg side of the lower cuff 20 forward, which applies to the knee joint of the patient a force of twisting toward the outer leg side, enabling reproduction of the correct screw-home movement every time the knee joint is extended.

Although the inclined grooves 37, 57 are respectively inclined with respect to the outer leg lower arm 35 and the inner leg lower arm 55, and the outer leg lower arm 35 and the inner leg lower arm 55 are respectively moved rearward and forward when the knee brace S1 is extended, thereby generating the outward twist along the screw-home movement of the normal knee joint in this embodiment, the means of generating the outward twist is not limited to this embodiment.

For example, the outward twist can be achieved by making the inclined groove 57 shorter than the inclined groove 37, thereby stopping the movement of the rotation fulcrum shaft 42 on the outer leg side earlier and then further continuing the movement of the rotation fulcrum shaft 59 on the inner leg side after the movement of the rotation fulcrum shaft 42 stops.

Moreover, the outward twist can also be achieved by making the upper end 54u side of the cam groove 54 on the outer leg side at a slightly lower position and slightly shorter than the cam groove 34 on the inner leg side, thereby stopping the movement of the cam shaft 62 earlier when extending the knee brace S1 and further continuing the movement of the cam shaft 39 after the movement of the cam shaft 62 stops.

Although this embodiment is configured, as shown in FIGS. 1 and 2, to arrange the outer leg lower arm 35 and the inner leg lower arm 55 on the side of contacting the leg and overlapping the outer leg upper arm 31 and the inner leg upper arm 51 on the outside of the outer leg lower arm 35 and the inner leg lower arm 55, respectively, the way of overlapping may be reversed to overlap the outer leg upper arm 31 and the inner leg upper arm 51 on the inside of the outer leg lower arm 35 and the inner leg lower arm 55, respectively.

Furthermore, by attaching the outer leg upper arm 31 and the inner leg upper arm 51 to the upper cuff 10 with the rivet 13 and removably attaching the outer leg lower arm 35 and the inner leg lower arm 55 to the lower cuff 20 with unsown bolts and nuts, right-and-left replacement of using the knee brace S1 for the right leg shown in FIG. 1 as a knee brace for the left leg and reassembling the knee brace S1 for bowleg shown in FIG. 1 into a knee brace for knock-knee will be possible. Thus, there is no need of manufacturing different parts for the right leg and the left leg, but the same part can be used for both the right leg and the left leg only by changing the direction of overlapping the arms 31, 35, 51, and 55.

While the knee brace S1 for correcting the bowleg on the right leg is configured so that the outer leg joint 30 contracts and the inner leg joint 50 extends when the knee is extended in this embodiment, the knee brace for correcting the bowleg on the left leg is similarly configured so that the outer leg joint mounted on the outside of the leg contracts and the inner leg joint mounted on the inner side of the leg extends.

Moreover, for the knee brace for correcting the knock-knee, an inner leg joint 30X and an outer leg joint 50X are attached to the upper cuff 10 and the lower cuff 20 so that the inner leg joint 30X contracts and the outer leg joint 50X extends.

Used as the knee brace for the knee osteoarthritis accompanied by knock-knee is symmetrical to the knee brace S1 shown in FIG. 1 with the inclined directions of the inclined grooves 37, 57 being reversed and the inclined direction of the inclined plane 55b being reversed.

Figure 12:
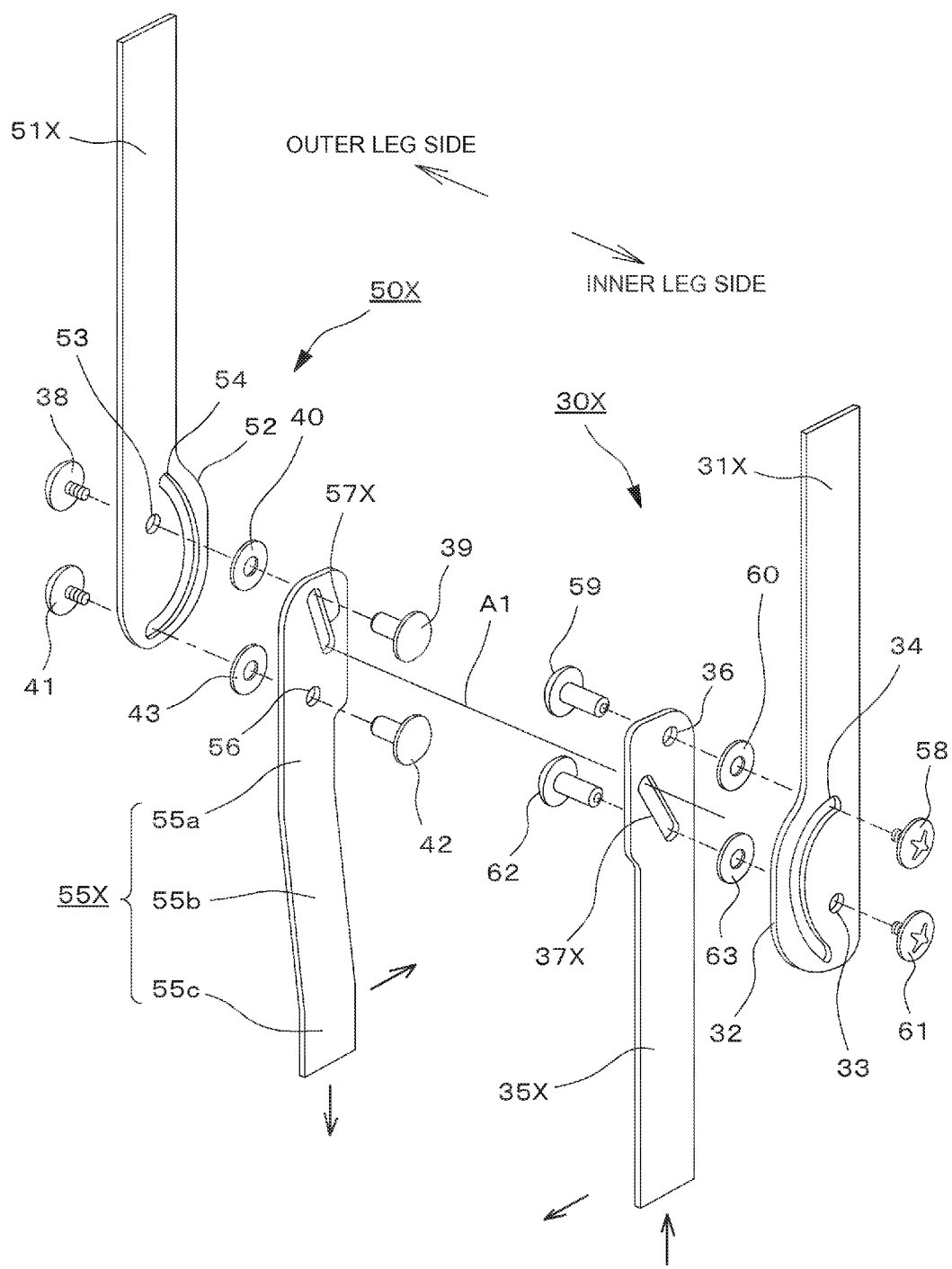
FIG. 12 is an illustration of the set of the outer leg joint and the inner leg joint for a knee osteoarthritis accompanied by knock-knee according to an embodiment of the present invention.

The inner leg joint 30X and the outer leg joint 50X of the knee for knock-knee are shown in FIG. 12. An inner leg upper arm 31X of the inner leg joint 30X is the same part as the outer leg upper arm 31 of the knee brace S1. An inner leg lower arm 35X has the same configuration as the outer leg lower arm 35 except that the inclined direction of an inclined groove 37X is reversed from the inclined groove 37. An outer leg upper arm 51X of the outer leg joint 50X is the same part as the inner leg upper arm 51 of the knee brace 51.

An outer leg lower arm 55X has the same configuration as the inner leg lower arm 55 except that the inclined direction of an inclined groove 57X is reversed from the inclined groove 57 and that the inclined direction of the inclined plane 55b is also reversed. Other configurations of the knee brace for knock-knee are same as those of the knee brace 51, and therefore the explanation thereof is omitted here.

When wearing the unshown knee brace for the knee osteoarthritis patient with knock-knee, in the state where the patient extends the knee, as shown in FIG. 11(C), the inner leg side of the crus 3 of the knee osteoarthritis patient with knock-knee is pulled up and the outer leg side is pushed down. This can correct the knock-knee in the direction of returning to the normal state of the knee as shown in FIG. 11(A).

Furthermore, because the knee osteoarthritis patient with knock-knee often has the cartilage on the outer leg side of the knee joint being worn and feels pain due to direct contact between bones, a space can be formed between the upper and lower bones of the knee joint on the outer leg side by pushing down the outer leg side of the crus 3, thereby reducing the pain due to the contact between the bones.

Although the knee brace S1 has the cam groove 34 provided in the outer leg upper arm 31 and the inclined groove 37 provided in the outer leg lower arm 35, the present invention can also be achieved by providing the inclined groove 37 in the outer leg upper arm 31 and the cam groove 34 in the outer leg lower arm 35. Similarly, although the cam groove 54 is provide in the inner leg upper arm 51 and the inclined groove 57 is provided in the inner leg lower arm 55 in this embodiment, the present invention can be achieved by providing the inclined groove 57 in the inner leg upper arm 51 and the cam groove 54 in the inner leg lower arm 55.

Thus, for example, even when the outer leg joint 30 and the inner leg joint 50 are fixed upside down to the upper cuff 10 and the lower cuff 20, the outer leg side of the lower cuff 20 is pulled upward and rearward and the inner leg side is pulled downward and forward, which is similar to the case of the knee brace S1 of this embodiment.

Because each of the arms 31, 35, 51, and 55 is constituted by a plate body, it is possible to provide the knee brace S1 that is thin and not bulky and that can be worn under pants.

Because each arm 31, 35, 51, and 55 has a simple geometry and can be produced in reinforced plastic, it is possible to provide the knee brace that is smooth and not causing a metallic sound at a low cost.

Although the knee brace S1 is provided with the inclined grooves 37, 57 to be inclined with respect to the lengthwise direction of the outer leg lower arm 35 and the inner leg lower arm 55, instead of the inclined grooves 37, 57, as shown in FIG. 13, longitudinal grooves 37', 57' may be provided in parallel with the lengthwise direction of the outer leg lower arm 35 and the inner leg lower arm 55. In this case, because the longitudinal grooves 37', 57' are not inclined, the outer leg lower arm 35 moves upward and the inner leg lower arm 55 moves downward when the patient extends the knee from the state of flexing at the right angle, which produces the correction effect on the bowleg.

Figure 14:
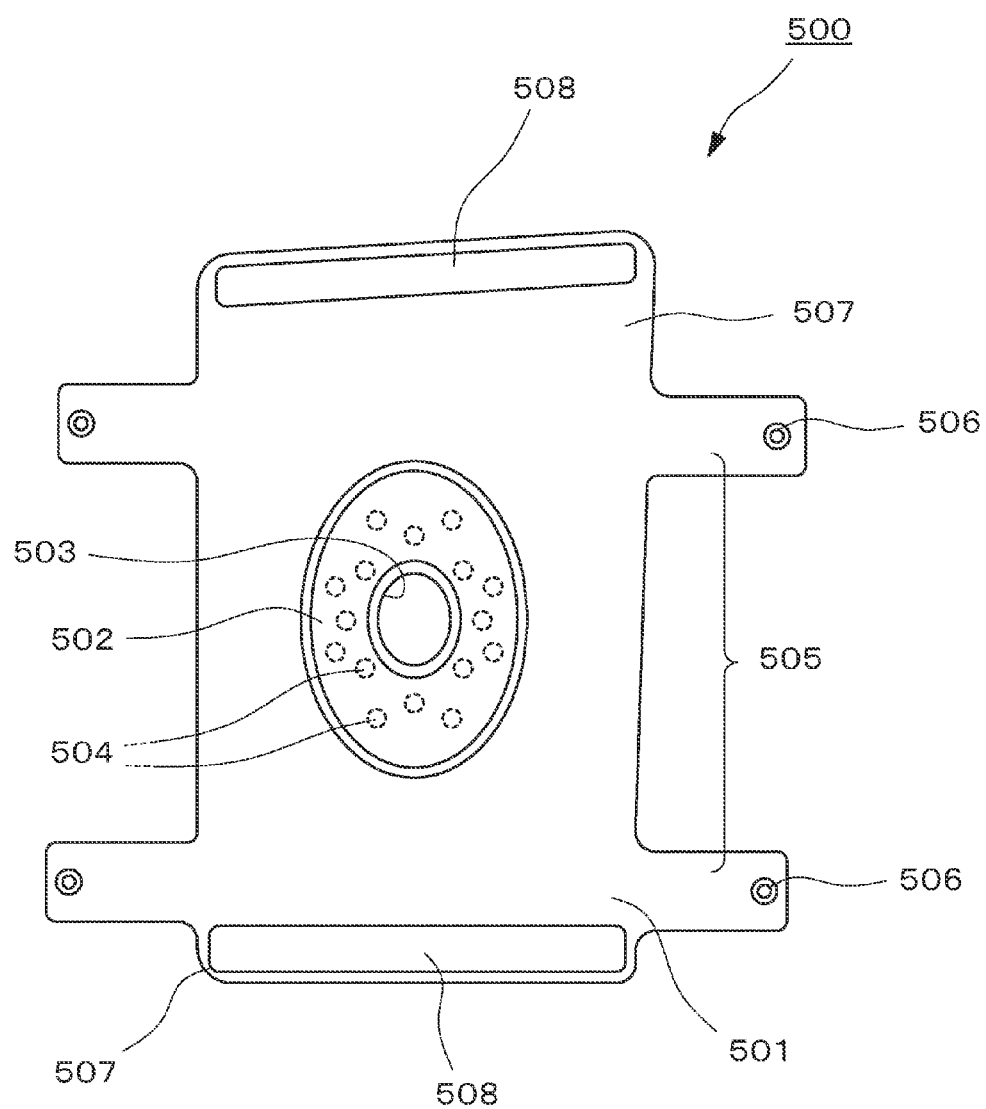
FIG. 14 is an illustration of a magnetic pad attachable to the knee brace according to the present invention.

A magnetic pad 500 shown in FIG. 14 may be fixed to the knee brace S1 to achieve the correction of the knee joint by the knee brace S1 and another effect of blood circulation promotion and the like by the magnetic pad 500 at the same time.

The magnetic pad 500 shown in FIG. 14 includes a covering 501 constituted by a stretchable fabric, a soft magnetic pad body 502 in a substantially oval shape formed by soft synthetic resin such as silicone rubber, and a strap 505 and an extension 507 for fixing the magnetic pad 500 to the knee brace S1.

A substantially circular opening 503 for adapting a kneecap is provided in the center of the magnetic pad body 502 therethrough. A plurality of known granular magnets 504 are embedded in a fixed manner at appropriate locations on the entire peripheral surface of the opening 503.

The magnetic pad body 502 is fixed at the substantial center of the covering 501 by fusing or sewing the entire periphery thereto.

The straps 505 are provided integrally on the right and left sides of the covering 501 two each arranged on top and bottom. A button 506 is fixed near a tip of each strap 505, which can fix each strap 505 to the outer leg joint 30 and the inner leg joint 50 by engaging with an unshown buttons provided in each of the outer leg upper arm 31, the outer leg lower arm 35, the inner leg upper arm 51, and the inner leg lower arm 55 of the knee brace S1.

The extensions 507 are provided to the top and bottom of the covering 501 for extending the length of the covering 501 in the upper and lower directions, respectively. To each of the extension 507, a hook-and-loop fastener 508 is attached, which can be adhered to a rear surface of each of the upper cuff 10 and the lower cuff 20 for fixing.

Figure 15:
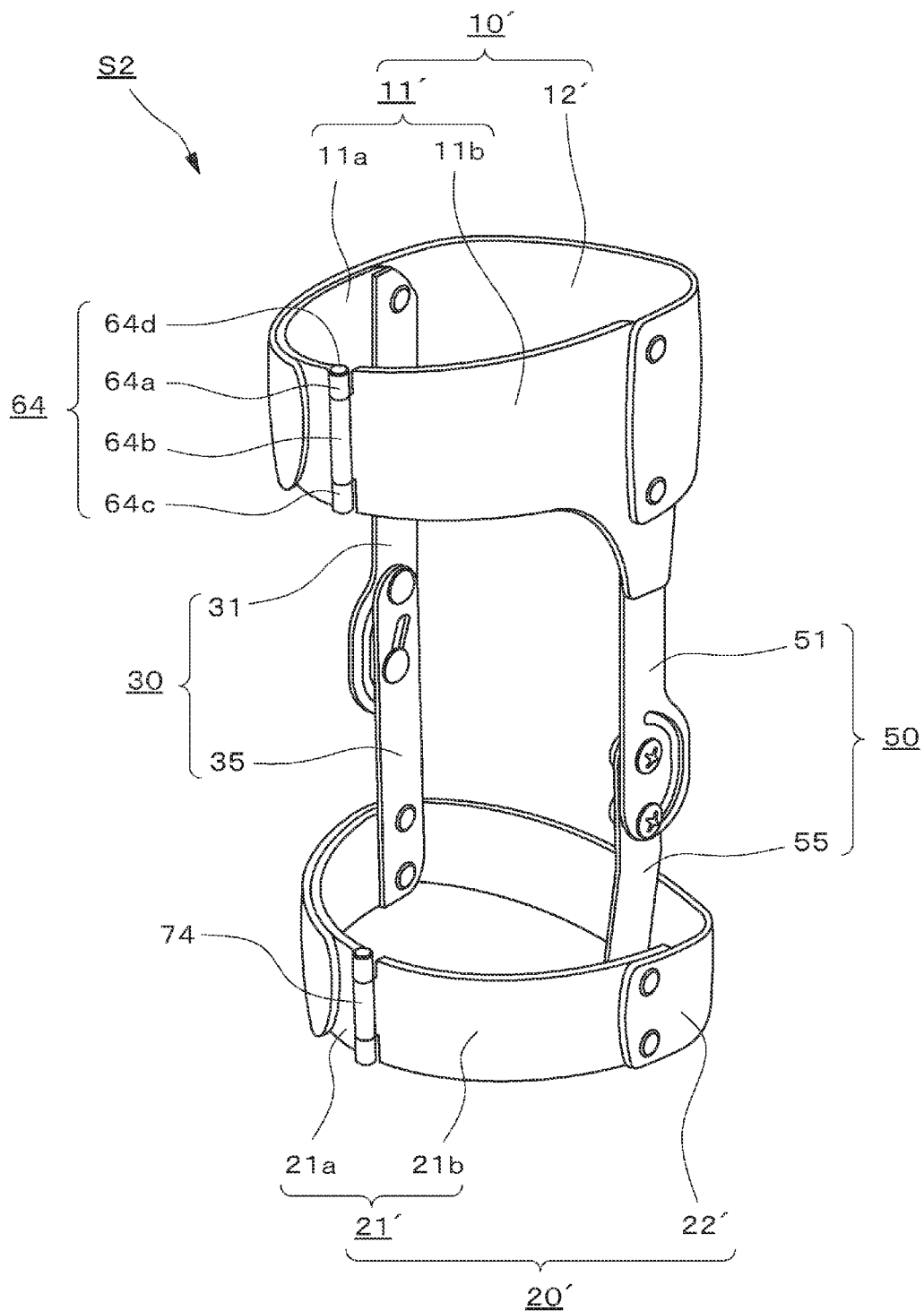
FIG. 15 is a perspective view of the knee brace according to another embodiment of the present invention.

Another embodiment of the present invention is shown in FIG. 15. A knee brace S2 shown in FIG. 15 is a foldable brace to be worn around the knee 2 of the knee osteoarthritis patient.

The knee brace S2 of this embodiment generally includes an upper cuff 10' fixed to the femur 1, a lower cuff 20' fixed to the crus 3, and the outer leg joint 30 and the inner leg joint 50 fixed to the upper cuff 10' and the lower cuff 20' at both ends and arranged on either side of the site peripheral to the knee joint of the patient. FIG. 15 depicts the knee brace S2 for the right leg of the bowleg patient.

The upper cuff 10' includes a substantially cylindrical femur support portion 11' made from a rigid material and an upper belt 12' fixed to one end side of the femur support portion 11' in the lateral direction. The femur support portion 11' includes an outer leg member 11a and an inner leg member 11b formed by dividing a substantially cylindrical shape curved around the front side of the femur 1 of the patient into right and left halves.

Provided between the outer leg member 11a and the inner leg member 11b is a hinge portion 64 that connects the outer leg member 11a and the inner leg member 11b in a foldable manner.

Figure 16:
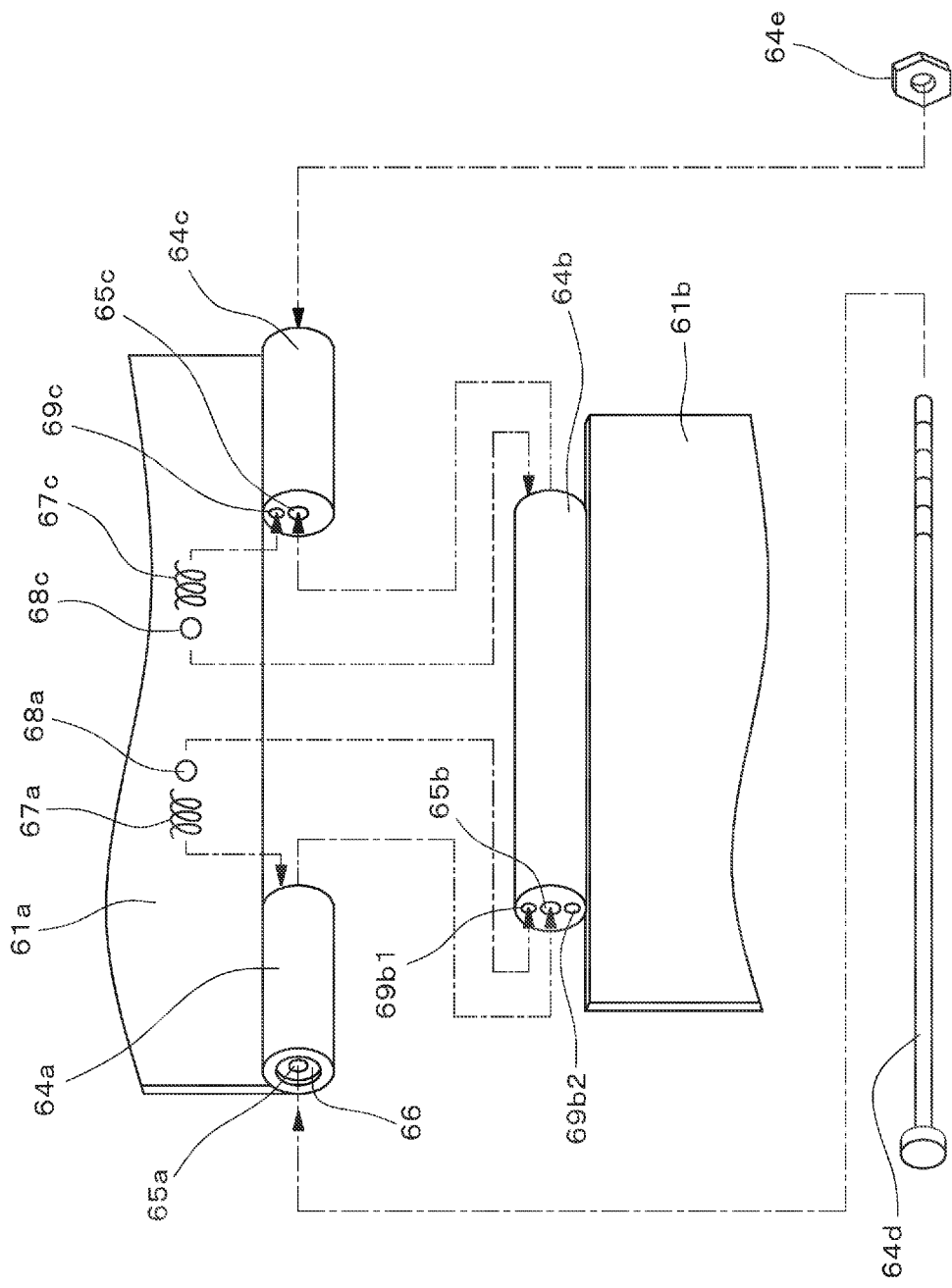
FIG. 16 is an illustration of a hinge portion of the knee brace shown in FIG. 15.

The hinge portion 64 includes, as shown in FIG. 16, a cylinder portion 64a, a cylinder portion 64b, a cylinder portion 64c, a pin 64d, and a stopper 64e. The cylinder portions 64a and 64c are formed integrally with an end portion of the outer leg member 11a on the knee center side, and the cylinder portion 64b is formed integrally with an end portion of the inner leg member 11b on the knee center side.

A through hole 65a is formed in the center of the cylinder portion 64a along a longitudinal direction thereof. A concave portion 66 for housing a head of the pin 64d is provided on one end of the cylinder portion 64a, and an unshown attachment for attaching a spring 67a is provided on the other end, respectively.

A through hole 65b is formed in the center of the cylinder portion 64b along a longitudinal direction thereof. Locking portions 69b1 and 69b2 capable of engaging with a portion of a spherical member 68a are provided at one end of the cylinder portion 64b. Provided at the other end are two unshown locking grooves capable of engaging with a portion of a spherical member 68c.

A through hole 65c is formed in the center of the cylinder portion 64c along a longitudinal direction thereof. An attachment 69c for attaching a spring 67c is provided at one end of the cylinder portion 64c, and an unshown concave portion for housing the stopper 64e is formed on the other end.

The spring 67a is attached to the unshown attachment of the cylinder portion 64a, and the spherical member 68a is further attached to the tip of the spring 67a. Moreover, the spring 67c is attached to the attachment 69c of the cylinder portion 64c, and the spherical member 68c is further attached to the tip of the spring 67c. In this state, the pin 64d is inserted in the through holes 65a, 65b, and 65c from the concave portion 66 side of the cylinder portion 64a with the tip of the pin 64d being stopped by the stopper 64e.

With this configuration, the hinge portion 64 foldably supports the outer leg member 11a and the inner leg member 11b. By moving the spherical members 68a, 68c between the locking grooves 69b1 and 69b2 and between the two unshown locking grooves provided on the other end of the cylinder portion 64b, the outer leg member 11a and the inner leg member 11b can be fixed alternatively to a deployed state and a folded state.

In other words, by holding the outer leg member 11a and the inner leg member 11b to separate from each other, the spherical members 68a and 68c move on both end surfaces of the cylinder portion 64b, engage with the locking groove 69b1 and the locking groove at the corresponding location on the other end surface of the cylinder portion 64b, get energized by the springs 67a, 67c, and thus the outer leg member 11a and the inner leg member 11b are fixed in the mutually deployed state.

By holding the outer leg member 11a and the inner leg member 11b to close them with respect to each other, the spherical members 68a and 68c move in opposite directions on both end surfaces of the cylinder portion 64b, engage with the locking groove 69b2 and the locking groove at the corresponding location on the other end surface of the cylinder portion 64b, get energized by the springs 67a, 67c, and thus the outer leg member 11a and the inner leg member 11b are fixed in the mutually folded state.

The lower cuff 20' includes a substantially semicylindrical crus support portion 21' made from a rigid material and a lower belt 22' fixed to one end side of the crus support portion 21' in a lateral direction. The crus support portion 21' includes an outer leg member 21a and an inner leg member 21b formed by dividing a substantially cylindrical shape curved around the front side of the crus 3 of the patient into right and left halves.

Provided between the outer leg member 21a and the inner leg member 21b is a hinge portion 74 configured like the hinge portion 64. The configuration and operation of the hinge portion 74 are same as those of the hinge portion 64, and therefore the explanation thereof is omitted here.

Other configurations of the knee brace S2 are same as those of the knee brace S1, and therefore the explanation thereof is also omitted here.

The knee brace S2 can be folded lengthwise by flexing the femur support portion 11' and the crus support portion 21' at the hinge portions 64, 74 and folding the upper belt 12' and the lower belt 22' formed by a soft material.

Figure 17:
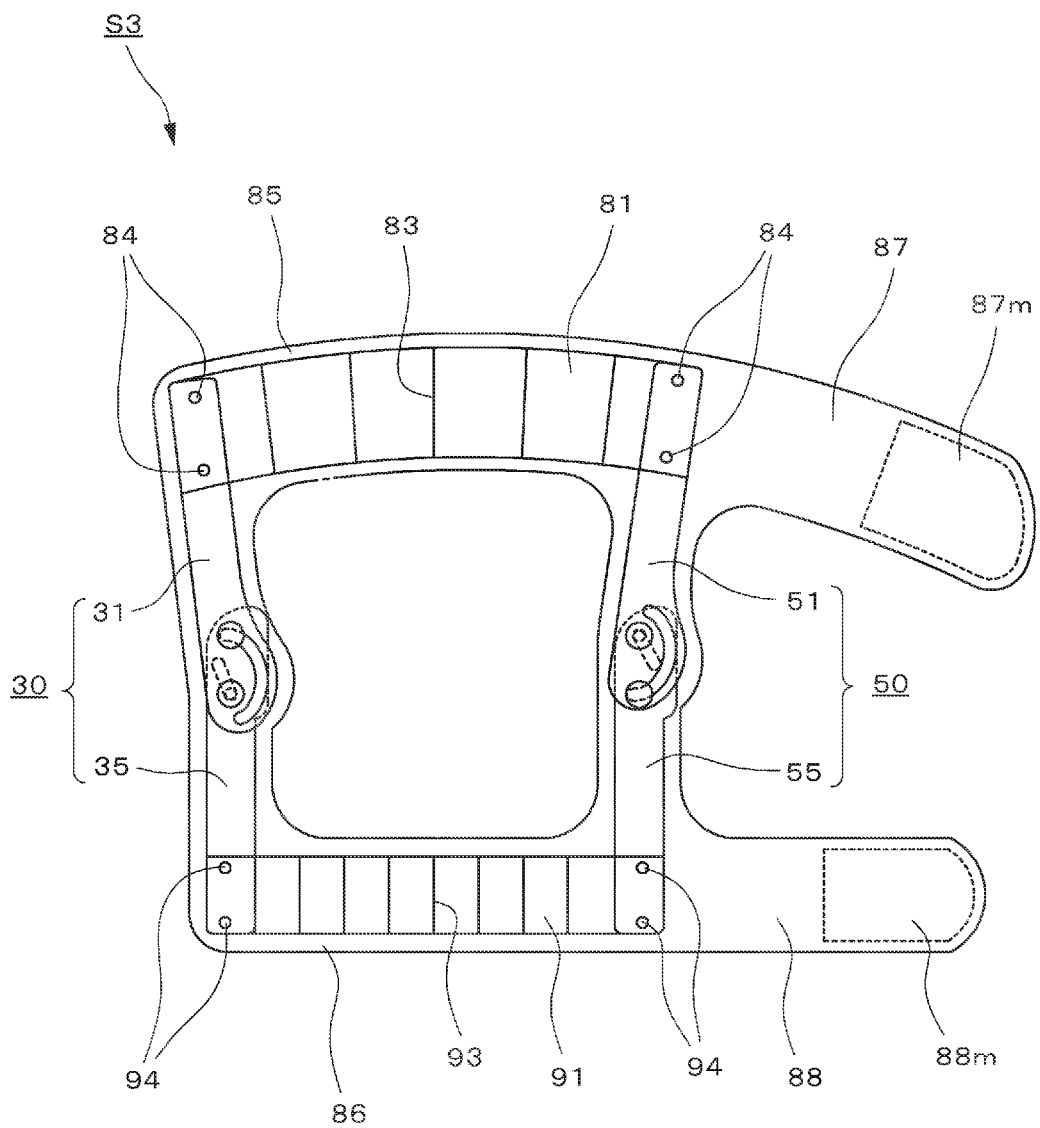
FIG. 17 is an illustration of the knee brace according to still another embodiment of the present invention.
Figure 18:
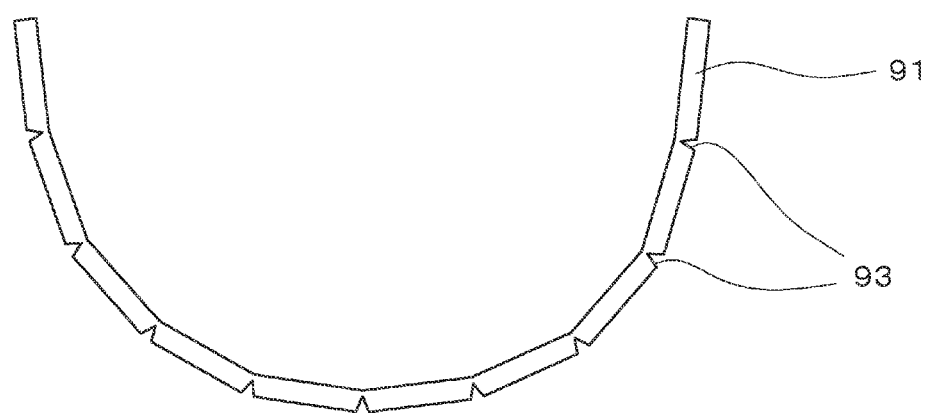
FIG. 18 is an illustration of a crus support member of the knee brace shown in FIG. 17.
Figure 20:
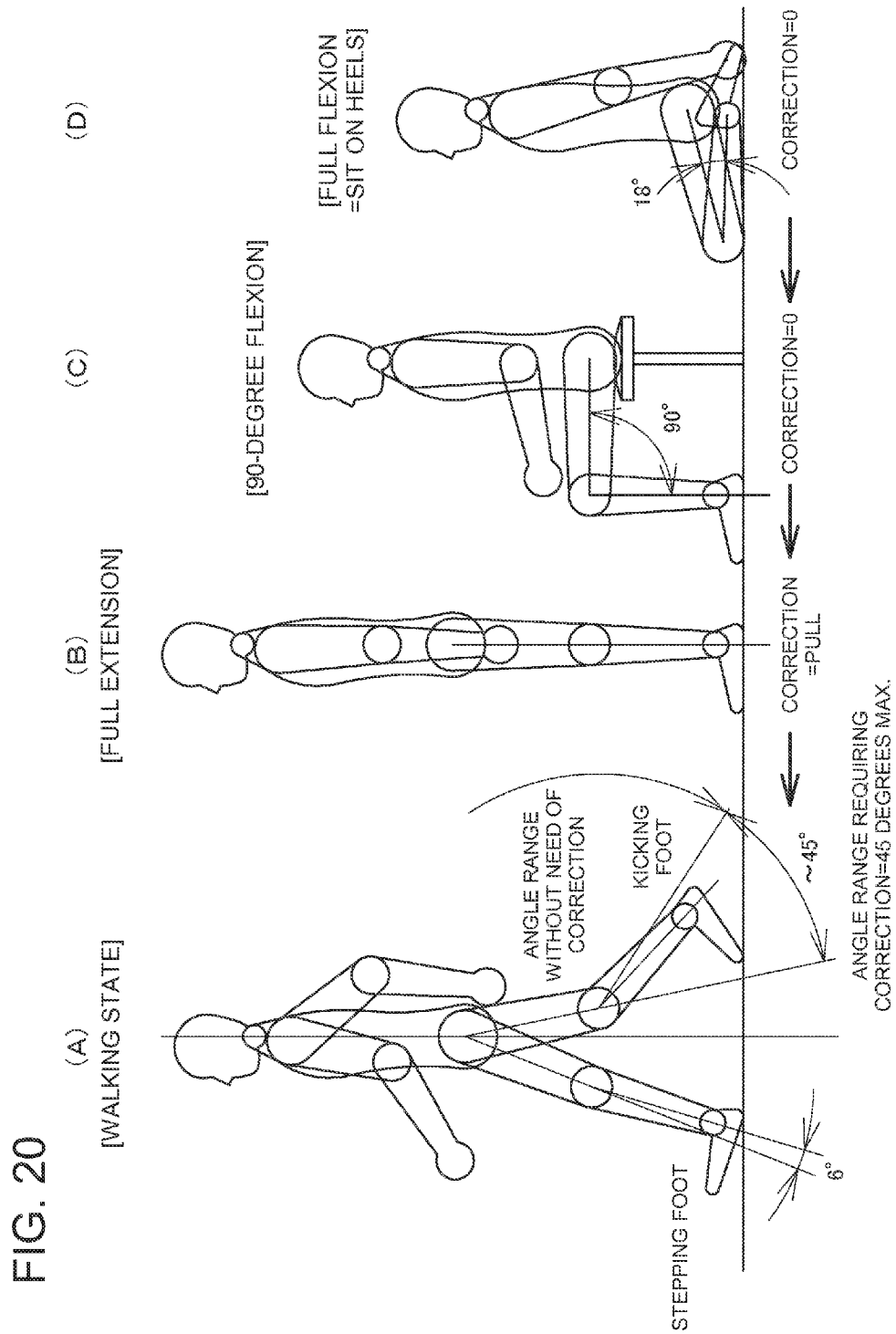
FIG. 20 is an illustration showing a relation between movement of a knee joint of a knee osteoarthritis patient accompanied by bowleg or knock-knee and an angle range requiring correction.

Although the knee brace S2 in FIG. 15 is configured to be foldable at the hinge portions 64, 74 as well as the upper belt 12' and the lower belt 22' by forming the femur support portion 11' and the crus support portion 21' from the rigid material, forming the hinge portions 64, 74, and forming the upper belt 12' and the lower belt 22' from the soft material, the knee brace may be made foldable, as show in FIGS. 17 and 18, by forming a plurality of notches 83, 93 in the femur support portion 11' and the crus support portion 21' in a longitudinal direction.

A knee brace S3 shown in FIG. 17 generally includes a femur support member 81 fixed to the femur 1 and a crus support member 91 fixed to the crus 3, each including a plate body made from a hard plastic, an outer leg joint 30 and an inner leg joint 50 fixed to the femur support member 81 and the crus support member 91 at both ends and arranged on either side of the site peripheral to the knee joint of the patient, and a cover 85 enveloping the femur support member 81, the crus support member 91, the outer leg joint 30, and the inner leg joint 50.

The femur support member 81 includes an elongated substantially rectangular plate body slightly curved with the center slightly convex upward, is provided with the plurality of notches 83 shown in FIGS. 17 and 18 on its surface opposite from the patient, and is configured to curve as shown in FIG. 18 by flexing along the femur 1.

The crus support member 91 includes an elongated rectangular plate body, is provided with the plurality of notches 93 shown in FIGS. 17 and 18 on its surface opposite from the patient, and is configured to curve by flexing along the crus 3 of the patient with the notches 93 facing outside. The number of the notches 93 in the crus support member 91 is smaller than the number of the notches 83 in the femur support member 81. This configuration enables a shape that fits the femur 1 and the crus 3 thinner than the femur 1.

The configurations of the outer leg joint 30 and the inner leg joint 50 are same as those in the knee brace S1, and therefore the explanation thereof is omitted here.

The femur support member 81 and the crus support member 91 are, as shown in FIG. 17, coupled to the outer leg joint 30 and the inner leg joint 50 by rivets 84 and 94.

The femur support member 81, the crus support member 91, the outer leg joint 30, and the inner leg joint 50 are covered by the cover 85 as they are coupled to one another.

The cover 85 is made from chloroprene rubber sponge, and includes a covering 86 that covers the femur support member 81, the crus support member 91, the outer leg joint 30, and the inner leg joint 50, a strap 87 extending on the inner leg side of the femur support member 81, and a strap extending on the inner leg side of the crus support member 91.

Hook-and-loop fasteners 87*m*, 88*m* are respectively fixed on the rear surface of the straps 87, 88, and thus the knee brace S3 is configured attachable to the patient by putting the straps 87, 88 from the back of the knee of the patient to the outer leg side and adhering the hook-and-loop fasteners 87*m*, 88*m* to the outer leg side surface of the femur support member 81 and the crus support member 91.

The femur support member 81 and the crus support member 91 may be formed in a shape of a watch band as shown in FIG. 19, instead of the plate body provided with the notches 83, 93. FIG. 19 shows a crus support member 91' formed in the shape of the watch band, which includes a plurality of band members 95 and a plurality of pins for coupling the band members 96. The band member 95 includes a plate body including a C-shaped portion 97 having a concave portion with its center cut out in a rectangular shape on one end side and a rectangular concave portion 98 formed slightly smaller than the concave portion on the other end side. The crus support member 91' includes the plurality of band members 95 coupled together by inserting the pin 96 through the C-shaped portion 97 of one band member 95 and the convex portion 98 of another band member 95.

An unshown femur support member in the shape of the watch band is configured similarly to the crus support member 91', and therefore the explanation thereof is omitted here.

The method of correcting the knee joint using the knee brace S1 performs, when receiving a force of pulling both ends of the outer leg joint and the inner leg joint so as to extend the knee from its flexed state, a procedure in which the cam shaft on the outer leg side slides from the lower end to a predetermined position in the cam groove on the outer leg side while the rotation fulcrum shaft on the outer leg side remains at the end portion on the knee side of the long groove on the outer leg side, and the cam shaft on the inner leg side slides from the upper end to a predetermined position in the cam groove on the inner leg side while the rotation fulcrum shaft on the inner leg side remains at the lower end of the long groove on the inner leg side, thereby deploying the flexion angles of the outer leg joint and the inner leg joint from an obtuse angle to the right angle, and a procedure in which the cam shaft on the outer leg side slides from a predetermined position to the upper end in the cam groove, the rotation fulcrum shaft on the outer leg side slides from the upper end on the inner leg side to the lower end in the long groove, the cam shaft on the inner leg side slides from a predetermined position on the inner leg side to the lower end in the cam groove, and the rotation fulcrum shaft on the inner leg side slides from the lower end on the inner leg side to the upper end in the long groove, thereby deploying the outer leg joint and the inner leg joint to their extended state. In this manner, when the outer leg joint and the inner leg joint extend, the second coupling means on the outer leg side moves upward and rearward, and the second coupling means on the inner leg side moves downward and forward, thereby pushing the knee joint of the patient toward the inner leg side and simultaneously twisting them toward the outer leg side.

The invention claimed is:

1. A knee brace comprising:
   a femur fixing element to be mounted on a femur of a patient;
   a crus fixing element to be mounted on a crus of the patient; and
   an outer leg joint and an inner leg joint, each of the outer leg joint and the inner leg joint fixed to the femur fixing element at a first end and fixed to the crus fixing element at a second end, the outer leg joint adapted to be arranged on an outer leg side of a knee joint of the patient and the inner leg joint adapted to be arranged on an inner leg side of the knee joint of the patient for flexing, wherein
   each of the outer leg joint and the inner leg joint includes a first coupling to be arranged along a side of the femur and a second coupling to be arranged along a side of the crus, the first coupling and the second coupling being coupled together by a coupling portion to be arranged at a side of the knee joint,
   the coupling portion includes a cam groove provided in the first coupling or the second coupling, a long groove provided in the second coupling or the first coupling, a rotation fulcrum shaft sliding in the long groove and provided in each of the first coupling or each of the second coupling, and a cam shaft sliding in the cam groove and provided to the second coupling or the first coupling, when the patient is standing such that the femur is substantially vertical, the cam groove on the outer leg side takes a curved shaped convex forward and the cam groove on the inner leg side takes a curved shape convex rearward with respect to the standing patient, wherein the rotation fulcrum shaft and the cam shaft slide in the long groove and the cam groove, respectively, when the patient flexes the knee, and thereby the second coupling rotates around the coupling portions with respect to the first coupling to flex the outer leg joint and the inner leg joint, wherein the rotation fulcrum shaft and the cam shaft slide in the long groove and the cam groove, respectively, when the outer leg joint and the inner leg joint extend, and thereby the second coupling on the outer leg side moves upward and rearward and the second coupling on the inner leg side moves downward and forward, and wherein the rotation fulcrum shaft of the outer leg joint is located at a front end portion of the long groove when the outer leg joint extends, and the rotation fulcrum shaft of the inner leg joint is located at a rear end portion of the long groove when the inner leg joint extends.

2. The knee brace according to claim 1, wherein
each cam groove is provided in the first coupling, each long groove is provided in the second coupling, each rotation fulcrum shaft is provided to the first coupling, and each cam shaft is provided to the second coupling,
the long groove on the outer leg side inclines with respect to a lengthwise direction of the second coupling, and
the long groove on the inner leg side inclines with respect to the lengthwise direction of the second coupling.

3. The knee brace according to claim 2, wherein
the long grooves on the outer leg side and the inner leg side incline with respect to the lengthwise direction of the second coupling so that a lower end is located anterior to an upper end,
the rotation fulcrum shaft on the outer leg side is located at the upper end of the long groove when the outer leg joint flexes substantially at a right angle and located at the lower end of the long groove when the outer leg joint extends, and
the rotation fulcrum shaft on the inner leg side is located at the lower end of the long groove when the inner leg joint flexes substantially at the right angle and located at the upper end of the long groove when the inner leg joint extends.

4. The knee brace according to claim 3, wherein
when the outer leg joint flexes to the right angle, a distance r2 from a point in the cam groove on the outer leg side where the cam shaft on the outer leg side is located to the rotation fulcrum shaft on the outer leg side and a distance r1 from a lower end of the cam groove on the outer leg side to the rotation fulcrum shaft on the outer leg side are substantially same as each other, and a distance r3 from an upper end of the cam groove on the outer leg side to the rotation fulcrum shaft on the outer leg side is longer than the distance r1 and the distance r2, and when the inner leg joint flexes at the right angle, a distance r5 from a point in the cam groove on the inner leg side where the cam shaft on the inner leg side is located to the rotation fulcrum shaft on the inner leg side and a distance r4 from the upper end of the cam groove on the inner leg side to the rotation fulcrum shaft on the inner leg side are substantially same as each other, and a distance r6 from the lower end of the cam groove on the inner leg side to the rotation fulcrum shaft on the inner leg side is longer than the distance r4 and the distance r5.

5. The knee brace according to claim 1, wherein
the femur fixing element and the crus fixing element include a rigid support portion supporting a part of each circumference of the femur and the crus and a soft coupling portion extending between both circumferential ends of the support portion, and
the support portion includes a folding portion extending in a lengthwise direction of the femur and the crus so that the support portion is foldable along the folding portion.

6. The knee brace according to claim 5, wherein
the folding portion includes a notch provided on an outer surface of the support portion and extending in the lengthwise direction of the crus.

7. The knee brace according to claim 5, wherein
the folding portion is formed by connecting adjacent band members with a pin.

8. A knee brace for a knee osteoarthritis patient accompanied by knock-knee comprising:
a femur fixing element to be mounted on a femur of the patient;
a crus fixing element to be mounted on a crus of the patient; and
an outer leg joint and an inner leg joint, each of the outer leg joint and the inner leg joint fixed to the femur fixing element at a first end and fixed to the crus fixing element at a second end, the outer leg joint adapted to be arranged on an outer leg side of a knee joint of the patient and the inner leg joint adapted to be arranged on an inner leg side of the knee joint of the patient for flexing, wherein
each of the outer leg joint and the inner leg joint include a first coupling to be arranged along a side of the femur and a second coupling to be arranged along a side of the crus, the first coupling and the second coupling being coupled together by a coupling portion to be arranged at a side of the knee joint,
the coupling portion includes a cam groove provided in the first coupling or the second coupling, a long groove provided in the second coupling or the first coupling, a rotation fulcrum shaft sliding in the long groove and provided to each of the first coupling or each of the second coupling, and a cam shaft sliding in the cam groove and provided to the second coupling or the first coupling,
when the patient is standing such that the femur is substantially vertical, the cam groove on the outer leg side takes a curved shaped convex rearward and the cam groove on the inner leg side takes a curved shape convex forward with respect to the standing patient,
wherein the rotation fulcrum shaft and the cam shaft slide in the long groove and the cam groove, respectively, when the patient flexes a knee, and thereby the second coupling rotates around the coupling portions with respect to the first coupling to flex the outer leg joint and the inner leg joint,
wherein the rotation fulcrum shaft and the cam shaft slide in the long groove and the cam groove, respectively, when the outer leg joint and the inner leg joint extend, and thereby the second coupling on the outer leg side moves downward and rearward and the second coupling on the inner leg side moves upward and forward, and wherein the rotation fulcrum shaft of the outer leg joint is located at a front end portion of the long groove when the outer leg joint extends, and the rotation fulcrum shaft of the inner leg joint is located at a rear end portion of the long groove when the inner leg joint extends.

9. A set of an outer leg joint and an inner leg joint of a knee brace that is fixed to a femur fixing element of the knee brace at a first end and a crus fixing element of the knee brace at a second end, the femur fixing element is adapted to be mounted on a femur of a patient and the crus fixing element is adapted to be mounted on a crus of the patient, the outer leg joint is adapted to be mounted on an outer leg side of a knee joint of the patient and the inner leg joint is adapted to be mounted on an inner leg side of the knee joint of the patient, and the outer leg joint and the inner leg joint are configured to be flexed on an outer side and an inner side of the knee joint, respectively, wherein
  each of the outer leg joint and the inner leg joint includes a first coupling to be arranged along a side of the femur and a second coupling to be arranged along a side of the crus, the first coupling and the second coupling being coupled together by a coupling portion to be arranged at the side of the knee joint,
  the coupling portion includes a cam groove provided in the first coupling or the second coupling, a long groove provided in the second coupling or the first coupling, a rotation fulcrum shaft sliding in the long groove and provided to each of the first coupling or each of the second coupling, and a cam shaft sliding in the cam groove and provided to the second coupling or the first coupling,
when the patient is standing such that the femur is substantially vertical, the cam groove on the outer leg side takes a curved shaped convex forward and the cam groove on the inner leg side takes a curved shape convex rearward with respect to the standing patient,
wherein the rotation fulcrum shaft and the cam shaft slide in the long groove and the cam groove, respectively, when the patient flexes a knee, and thereby the second coupling rotates around the coupling portions with respect to the first coupling to flex the outer leg joint and the inner leg joint,
wherein the rotation fulcrum shaft and the cam shaft slide in the long groove and the cam groove, respectively, when the outer leg joint and the inner leg joint extend, and thereby the second coupling on the outer leg side moves upward and rearward and the second coupling on the inner leg side moves downward and forward, and
wherein the rotation fulcrum shaft of the outer leg joint is located at a front end portion of the long groove when the outer leg joint extends, and the rotation fulcrum shaft of the inner leg joint is located at a rear end portion of the long groove when the inner leg joint extends.

* * * * *